United States Patent [19]
Gold

[11] Patent Number: 5,844,110
[45] Date of Patent: Dec. 1, 1998

[54] SYNTHETIC TRIPLE HELIX-FORMING COMPOUND PRECURSORS

[75] Inventor: Barry I. Gold, Plattsmouth, Nebr.

[73] Assignee: University of Nebraska Board of Regents, Omaha, Nebr.

[21] Appl. No.: 384,324

[22] Filed: Feb. 1, 1995

[51] Int. Cl.$^6$ .......................... C07H 7/06; C07D 239/72; C07D 471/00; C07D 487/00
[52] U.S. Cl. ..................... 536/29.2; 536/27.13; 544/279; 544/283
[58] Field of Search .................................. 536/23.1, 24.5, 536/26.7, 29.2; 544/279, 283

[56] References Cited

U.S. PATENT DOCUMENTS

| | | | |
|---|---|---|---|
| 5,064,833 | 11/1991 | Ife et al. ................................... | 514/260 |
| 5,187,168 | 2/1993 | Primeau et al. ......................... | 514/259 |
| 5,539,082 | 7/1996 | Nielson et al. .......................... | 530/300 |

OTHER PUBLICATIONS

Neilson et al. (II), "Sequence–Selective Recognition Of DNA By Strand Displacement with a Thymine–Substituted Polyamide," *Science*, 254(5037), 1497–1500 (Dec. 6, 1991).
Egholm et al. (I), "Recognition Of Guanine And Adenine In DNA By Cytosine And Thymine Containing Peptide Nucleic Acids (PNA)," *J. Amer. Chem. Soc.*, 114(24), 9677–9678 (Nov. 18, 1992).
Egholm et al. (II), "Peptide Nucleic Acids Containing Adenine Or Guanine Recognize Thymine and Cytosine in Complementary DAN Sequences," *J. Chem. Soc., Chem. Comm.*, (9), 800–801 (May 7, 1993).
Egholm et al. (III), "Peptide Nucleic Acids (PNA). Oligonucleotide Analogues With An Achiral Peptide Backbone," *J. Am. Chem. Soc.*, 114(5), 1895–1897 (Feb. 26, 1992).
Egholm et al. (IV), "PNA Hybridizes To Complementary Oligonucleotides Obeying The Watson–Crick Hydrogen Bonding Rules," *Nature*, 365, 566–568 (Oct. 7, 1993).
Gura, "Antisense Has Growing Pains—Efforts to Develop Antisense Compounds for Cancer, AIDS, and Other Diseases Have Encountered Some Unexpected Questions About How the Drugs Really Work,", *Science*, 270, 575–577 (1995).
Krieg et al., "CpG Motifs in Bacterial DNA Trigger Direct B–Cell Activation," *Nature*, 374, 546–549 (6 Apr. 1995).
Ireland et al., "An Efficient Method for the Preparation of Furanoid and Pyranoid Glycals," *J. Org. Chem.*, 43(8), 786–787 (1978).
Maher et al., "Kinetic Analysis of Oligodeoxyribonucleotide–Directed Triple–Helix Formation on DNA," *Biochemistry*, 29(37), 8820–8826 (1990).

Birg et al., Nucleic Acids Research 18:2901 (1990).
Borowiec et al., Cell 60:181 (1990).
Challberg and Kelly, Ann. Rev. Biochem. 58:671 (1989).
Chen and Sigman, J. Amer. Chem. Soc. 110:6570 (1988).
Chen and Sigman, Proc. Natl. Acad. Sci. USA 83:7147 (1986).
Cheng et al., J. Org. Chem. 50:2778 (1985).
Cohen, J.S., et al., Scientific American, Dec. 1994, pp. 76–82.
Cooney et al., Science 241:456 (1988).
Farr et al., J. Org. Chem. 57:2093 (1992).
Farr et al., Carbohydrate Chemistry 9:653 (1990).
Francois et al., Proc. Natl. Acad. Sci. USA 86:9702 (1989).
Gao and Jones, J. Am. Chem. 109:1275 (1987).
Gish and Eckstein, Science 240:1520 (1988).
Horne and Dervan, J. Amer. Chem. Soc. 112:2435 (1990).
Jayasena and Johnston, Nucleic Acids Research 20:5279 (1992).
Jeffery and Takagi, Acc. Chem. Res. 11:264 (1978).
Jung and Lyster, J. Org. Chem. 42:3761 (1977).
Li and Kelly, Proc. Natl. Acad. Sci. USA 81:6973 (1984).
Minamikawa and Brossi, Tetrahedron Lett. No. 34:3085 (1978).
Ness, J. Org. Chem. 26:2895 (1961).
Rhode, S., J. Virol. 54:630 (1985).
Schreiber et al., Nucl. Acid Res. 13:7663 (1985).
Stein et al., Nucleic Acids Research 16:3209 (1988).
Stein et al., Anal. Biochem. 188:11 (1990).
Stillman et al., EMBO J. 4:2933 (1985).
Strobel et al., J. Amer. Chem. Soc. 110:7927 (1988).
Takusagawa, J. Biomolec. Struct. Dyn. 7:795 (1990).
Thuong and Chassignol, Tetrahedron Lett. 29:5905 (1988).
Saenger, Principles of Nucleic Acid Structure, p. 123, Springer Verlag, NY (1988).
Zhang and Davies, J. Org. Chem. 57:4690 (1992).
Wold et al., Proc. Natl. Acad. Sci. USA 84:3643 (1987).
Simmons et al., J. Virol. 64:1973 (1990).
Manzini et al., J. Mol. Biol. 213:833 (1990).

*Primary Examiner*—John Kight
*Assistant Examiner*—L. Eric Crane
*Attorney, Agent, or Firm*—Dann, Dorfman, Herrel and Skillman

[57] ABSTRACT

The present invention discloses novel monomeric compositions which are substituted quinoline- or quinazoline-based structures capable of hydrogen bonding specifically with interstrand purine-pyrimidine base pairs in a double-stranded Watson-Crick DNA molecule. Furthermore, the novel monomeric compounds of the present invention are capable of being assembled in specific sequences into oligomers capable of binding with sequence specificity to duplex DNA via a triple helix motif.

6 Claims, 20 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: YES

-continued (i v) ANTI-SENSE: NO (x i) SEQUENCE DESCRIPTION: SEQ ID NO:1:

AATCTTTTCT TTTTTCTTTT GTAATAGTGT         30

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: YES (i v) ANTI-SENSE: YES (x i) SEQUENCE DESCRIPTION: SEQ ID NO:2:

TTTTCTTTTT TCTTTTCT         18

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: double
        (D) TOPOLOGY: Not Relevant (i i) MOLECULE TYPE: DNA (genomic)

(i i i) HYPOTHETICAL: YES (i v) ANTI-SENSE: NO (x i) SEQUENCE DESCRIPTION: SEQ ID NO:3:

AGGAAAGAAA AAGCTTTCTT TCTGACGGAC         30

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: YES (i v) ANTI-SENSE: YES (x i) SEQUENCE DESCRIPTION: SEQ ID NO:4:

TCTTTCTTTT TTTTCTTT         18

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: double
        (D) TOPOLOGY: Not Relevant (i i) MOLECULE TYPE: DNA (genomic)

(i i i) HYPOTHETICAL: NO (i v) ANTI-SENSE: NO (v i) ORIGINAL SOURCE:
        (A) ORGANISM: SV40

( v i i i ) POSITION IN GENOME:
            ( A ) CHROMOSOME/SEGMENT: EARLY PALIDROME ( x i ) SEQUENCE DESCRIPTION: SEQ ID NO:5:

CACTACTTCT GGATAGCTC                                                                                              19

( 2 ) INFORMATION FOR SEQ ID NO:6:

( i ) SEQUENCE CHARACTERISTICS:
                ( A ) LENGTH: 24 base pairs
                ( B ) TYPE: nucleic acid
                ( C ) STRANDEDNESS: double
                ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: SV40

( v i i i ) POSITION IN GENOME:
            ( A ) CHROMOSOME/SEGMENT: CENTRAL REGION ( x i ) SEQUENCE DESCRIPTION: SEQ ID NO:6:

AGAGGCCGAG GCGGCCTCGG CCTC                                                                                        24

( 2 ) INFORMATION FOR SEQ ID NO:7:

( i ) SEQUENCE CHARACTERISTICS:
                ( A ) LENGTH: 18 base pairs
                ( B ) TYPE: nucleic acid
                ( C ) STRANDEDNESS: double
                ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: PARVOVIRUS ( x i ) SEQUENCE DESCRIPTION: SEQ ID NO:7:

GTATGTAACG TTCCAGGA                                                                                               18

( 2 ) INFORMATION FOR SEQ ID NO:8:

( i ) SEQUENCE CHARACTERISTICS:
                ( A ) LENGTH: 18 base pairs
                ( B ) TYPE: nucleic acid
                ( C ) STRANDEDNESS: double
                ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: PARVOVIRUS ( x i ) SEQUENCE DESCRIPTION: SEQ ID NO:8:

ACGACGAAGC TTACGCTG                                                                                               18

( 2 ) INFORMATION FOR SEQ ID NO:9:

( i ) SEQUENCE CHARACTERISTICS:
    ( A ) LENGTH: 14 base pairs
    ( B ) TYPE: nucleic acid
    ( C ) STRANDEDNESS: double
    ( D ) TOPOLOGY: Not Relevant ( i i ) MOLECULE TYPE: DNA (genomic)

( i i i ) HYPOTHETICAL: NO ( v i ) ORIGINAL SOURCE:
    ( A ) ORGANISM: PARVOVIRUS ( v i i i ) POSITION IN GENOME:
    ( A ) CHROMOSOME/SEGMENT: P4 TATA BOX ( x i ) SEQUENCE DESCRIPTION: SEQ ID NO:9:

CTGTATATAA GCAG    14

( 2 ) INFORMATION FOR SEQ ID NO:10:

( i ) SEQUENCE CHARACTERISTICS:
    ( A ) LENGTH: 14 base pairs
    ( B ) TYPE: nucleic acid
    ( C ) STRANDEDNESS: double
    ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: SV40

( v i i i ) POSITION IN GENOME:
    ( A ) CHROMOSOME/SEGMENT: EARLY PROMOTER ( x i ) SEQUENCE DESCRIPTION: SEQ ID NO:10:

TATTTATGCA GAGG    14

( 2 ) INFORMATION FOR SEQ ID NO:11:

( i ) SEQUENCE CHARACTERISTICS:
    ( A ) LENGTH: 15 base pairs
    ( B ) TYPE: nucleic acid
    ( C ) STRANDEDNESS: double
    ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: PARVOVIRUS ( v i i i ) POSITION IN GENOME:
    ( A ) CHROMOSOME/SEGMENT: P38 TATA BOX ( x i ) SEQUENCE DESCRIPTION: SEQ ID NO:11:

CTCCTATAAA TTCGC    15

( 2 ) INFORMATION FOR SEQ ID NO:12:

( i ) SEQUENCE CHARACTERISTICS:
    ( A ) LENGTH: 15 base pairs
    ( B ) TYPE: nucleic acid
    ( C ) STRANDEDNESS: double
    ( D ) TOPOLOGY: Not Relevant ( i i ) MOLECULE TYPE: DNA (genomic)

(i i i) HYPOTHETICAL: NO (i v) ANTI-SENSE: NO (v i) ORIGINAL SOURCE:
    (A) ORGANISM: PARVOVIRUS (v i i i) POSITION IN GENOME:
    (A) CHROMOSOME/SEGMENT: P38 TAR ELEMENT (x i) SEQUENCE DESCRIPTION: SEQ ID NO:12:

TTGGTTGGTG AAGAA                                                    15

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: double
        (D) TOPOLOGY: Not Relevant (i i) MOLECULE TYPE: DNA (genomic)

(i i i) HYPOTHETICAL: NO (i v) ANTI-SENSE: NO (v i) ORIGINAL SOURCE:
        (A) ORGANISM: VACCINIA VIRUS (x i) SEQUENCE DESCRIPTION: SEQ ID NO:13:

CAGTTCTAAA AATGATAAGC G                                             21

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: double
        (D) TOPOLOGY: Not Relevant (i i) MOLECULE TYPE: DNA (genomic)

(i i i) HYPOTHETICAL: NO (i v) ANTI-SENSE: NO (v i) ORIGINAL SOURCE:
        (A) ORGANISM: VACCINIA VIRUS (x i) SEQUENCE DESCRIPTION: SEQ ID NO:14:

CTACTGTCTA TTCAGTTGAC                                               20

SYNTHETIC TRIPLE HELIX-FORMING COMPOUND PRECURSORS

FIELD OF THE INVENTION

The present invention relates to novel synthetic monomers that have the capacity to be assembled into defined oligomers which bind with sequence specificity to duplex Watson-Crick DNA via a triple helix motif. More particularly, the present invention discloses novel monomer molecules which, when assembled into defined oligomeric sequences, may be used for a variety of purposes related to target-specific control of gene expression.

BACKGROUND OF THE INVENTION

One of the most important features of the classical DNA molecule is that it usually consists of two complementary polymeric strands twisted about each other in the form of a regular right-handed double helix. Each strand is a polynucleotide, i.e. a polymeric collection of four different types of nucleotide bases in which the sugar moiety of each nucleotide is linked by a phosphate group to the sugar moiety of an adjacent nucleotide. In a DNA Molecule, each nucleotide contains a deoxyribose residue, a phosphate group and a purine or pyrimidine base. There are two different single-ringed pyrimidines, thymine ("T") and cytosine ("C"), and two different double-ringed purines, which are adenine ("A") and guanine ("G"). In the polynucleotide DNA strand, the sugar and phosphate groups are always linked together by the same chemical bonds, known in the art as 3'-to-5'phosphodiester linkages. Hence, this part of the DNA molecule, called the sugar-phosphate backbone, is very regular. In contrast, the order of the purine and pyrimidine bases along a single strand of the DNA molecule is highly irregular, varying from one DNA molecule to another. Both the purine and the pyrimidine bases are flat, relatively water-insoluble molecules that tend to stack above each other at an angle shifted no more than about 25 degrees from perpendicular to the long axis of the double-stranded DNA helix, the shift being the result of natural tilt and propeller twist of the purine and pyrimidine bases.

The two complementary strands of the DNA double helix are joined by interstrand hydrogen bonding between complementary pairs of nucleotide bases. An adenine (A) nucleotide base on one strand of the helix is always paired by hydrogen bonding with a thymine (T) nucleotide on the opposite strand, thereby forming an interstrand adenine→thymine or thymine→adenine base pair (A—T or T—A, respectively). In like manner, a guanine (G) moiety on one strand is always paired with a cytosine (C) moiety on the opposite strand, thereby forming an interstrand guanine→cytosine or cytosine→guanine base pair (G—C or C—G, respectively). These are the only pairings that occur with the natural nucleotide bases. The strictness of this pairing creates complementary sequences of bases on the two intertwined strands. Thus, if the nucleotide sequence on one strand of the DNA double helix is the "sense" or "positive" strand sequence, then the nucleotide sequence on the opposite strand will be exactly complementary (according to the base pairing rules just cited) and is the "antisense" or "negative" strand sequence.

Because the glycosidic bonds that attach the paired nucleotide bases to their respective sugar rings do not lie directly opposite each other, the sugar-phosphate backbones of the double helix are not equally spaced along the helical axis. This results in the formation of a "major" (wider) and a "minor" (narrower) helical groove in the B-DNA double helix. B-DNA and closely related forms are the predominant class of DNA found in physiologic conditions.

The availability of the wider spacing in the major groove in the duplex DNA molecule is of central importance to the usefulness of the novel compounds of the present invention. The hydrogen-bonding potential associated with the major groove shows much greater dependence on nucleotide base sequence than does the minor groove and, therefore, outside molecules (such as proteins or synthetic "antisense" oligomers), which are influenced by nucleotide base sequence, form hydrogen bonds predominantly to specific groups positioned in the major groove. These concepts are well known in the art, and are summarized in standard reference textbooks such as that of Watson et al., *Molecular Biology of the Gene* (Fourth Edition), The Benjamin/Cummings Publishing Company, Inc., Menlo Park, Calif., 1987.

Triple Helix.

Triple helix structures, first reported in 1957 from the combination of poly-adenylic acid ("poly-A") with two equivalents of poly-uridylic acid ("poly-U") (Felsenfeld et al., J. Amer. Chem. Soc. 79: 2023, 1957), have recently attracted a great deal of chemical and biological interest. It is known that the third pyrimidine strand, which resides in the major groove of duplex DNA, recognizes homopurine stretches and binds parallel to the purine strand (referred to as "parallel motif" or "pyrimidine motif" as shown in FIG. 1). There is also evidence that the triple helix ("triplex") structures so generated adopt the A-form of DNA (normally found in unhydrated DNA) with the associated sugar puckers (C3'-endo conformation) and positive base pair tilt. In another approach, which uses purines in the third strand, the recognition of the purine stretch in the duplex is anti-parallel (referred to as "purine motif" or "anti-parallel motif").

The formation of a parallel motif triplex structure with a G—C base pair usually requires protonation of the N3-cytosine position so that hydrogen bonding to $O^6$-guanine is possible (FIG. 1). This is favored at a pH less than 7.0, although triplex formation with oligomers containing 5-methyl cytosine residues is less dependent on low pH. Thermodynamic studies have shown that the average change in ethalphy is approximately −6.6 kcal/mol of binding pyrimidine and that the major factors contributing to third strand binding are base stacking and hydrogen bonding interactions (Manzini et al., J. Mol. Biol. 213: 833, 1990). Protonation is not required when the third strand uses the purine motif.

Another usual requirement for traditional triplex structure formation at near physiological pH has been that the third strand oligomer be charged. This is confirmed by observations that neutral oligomers such as the methylphosphonates do not form stable triplex structures with DNA. In order to achieve the desired charged backbone structure, the third strand oligomer (being an "oligonucleotide") is usually synthesized to contain a phosphodiester backbone. However, oligonucleotides with phosphodiester backbones have been limited in their utility as antisense molecules because of the significant nuclease susceptibility of the phosphodiester linkages.

Furthermore, the general requirement for homogeneous runs of purine/pyrimidine nucleotide bases in the formation of a traditional triple helix structure has resulted from the need to use natural nucleotide bases in the complementary third strand, due to the unavailability of any other molecules to substitute effectively for these natural bases. Traditional third strand binding has therefore been restricted to homogeneous runs of natural purines or pyrimidines because of spacial restrictions associated with Hoogsteen base pairing of the $N^7$- and $X^6$-positions of naturally occurring purines (X is the $NH_2$ or oxygen for adenine and guanine, respectively) in the homopurine strand of the Watson-Crick duplex DNA. Because only the homopurine strand of the duplex provides hydrogen bonding information in such a structure, the third strand binds asymmetrically in the major groove nearest to the sugar-phosphate backbone of the purine strand (FIG. 1). As a result, any deviation from homopurine sequence requires that the traditional third strand actually cross over to the other side of the major groove (FIG. 2). Limitations in the span and flexibility of the 5'-3'-linked deoxyribose/phosphodiester backbone do not allow this to occur. Thus, any pyrimidine interruption in the homopurine strand cannot be accommodated by the traditional third strand and also significantly destabilizes traditional triple helix formation.

In addition to the crossover barrier, the major groove hydrogen-bonding information on the purine molecule targeted by the third strand is not the same for A—T as compared to T—A pairing (FIG. 3). As seen in FIG. 3, the open arrows containing the letter "A" indicate the hydrogen bond acceptor atoms, and the open arrows containing the letter "D" indicate the hydrogen bond donor atoms. The N7-adenine hydrogen bond acceptor and $N^6H_2$-adenine hydrogen bond donor are reversed for A—T relative to T—A pairing as viewed facing the major groove. This is equivalent to the thymine (T) of the third strand flipping as if the orientation of the strand changed from 3'-5' to 5'-3'. As a result, the design of therapies based on the traditional triple helix motif would be drastically limited to reasonably-sized homopurine/homopyrimidine regions of genes. The number of guanine moieties in the homopurine strand is also limited because of the requirement that, in order to bind, cytosines of the third strand must be protonated at physiological pH, which they cannot be. These are fatal limitations in the prior art technology.

Attempts have been made to circumvent these problems. Recently, an oligomer containing both a single 3'-3'-linked oligonucleotide and a 1, 2-dideoxy-D-ribose linker has been prepared which can accommodate the major groove crossover and recognizes 5'-$A_3GA_5G$-$CT_3CT_3CT$ (Horne & Dervan, J. Amer. Chem. Soc. 112: 2435, 1990) (FIG. 2).

In stark contrast to the traditional triple helix motifs which require homogenous stretches of either purine or pyrimidine nucleotide bases as targets for binding, the synthetic oligomeric molecules of the present invention permit any known duplex DNA and/or RNA sequences to be targeted, including the usual duplex DNA and/or RNA sequences which contain heterogeneous (mixed) sequences of purines and pyrimidines. Synthetic oligomers containing these novel bases recognize major-groove hydrogen bonding information associated with the purine and, optionally, the pyrimidine bases contained in each interstrand nucleotide base-pair combination in the targeted gene sequence. Moreover, the orientation of the backbone of these oligomers enables them to fit the major groove of a mixed purine-pyrimidine duplex. Consequently, oligomers comprising the synthetic monomeric compound of this invention form stable sequence-specific triple helix structures with duplex (double-stranded) Watson-Crick DNA molecules, and do so in such a way that the sugar-phosphate backbone of the synthetic oligomer lies near the center of the major groove of the duplex DNA structure. Because these novel oligomers recognize nucleotide base sequences in double-stranded DNA without the limitation that the binding be done at low pH, or that the targeted sequence be only a homogeneous sequence of either purines or pyrimidines, the construction of triple helix-forming oligomers directed against any known heterogeneous sequence of purines and pyrimidines (as is commonly found in viral or non-viral sequences) is straightforward.

SUMMARY OF THE INVENTION

In accordance with this invention, there are provided novel triple helix-forming oligomers wherein the nucleotide monomeric units are comprised of certain carefully designed quinoline and quinazoline residues (comprising a quinoline or quinazoline base moiety, an attached sugar component, and an attached phosphate component). These novel residue units can be grouped according to which of the interstrand G—C, C—G, A—T or T—A nucleotide base pairings in a targeted duplex DNA molecule the compounds bind. The specificity of binding by the novel monomers is dictated by the spatial arrangement of hydrogen-bond acceptor and hydrogen-bond donor sites of the interstrand G—C, C—G, A—T or T—A nucleotide base pairs.

According to one aspect of the present invention, a substituted quinazoline having the following formula is provided:

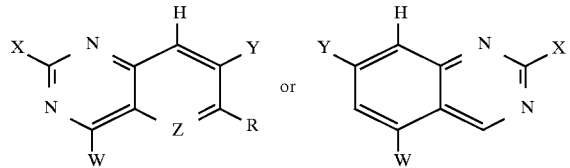

wherein X and Y are the same or different and are selected from the group consisting of—NRR', —OR, and —SR and; Z represents C—R =C—R and =N—R; R and R' are the same or different and are selected from the group consisting of hydrogen, lower-alkyl, carboxyl and $C_6$–$C_{12}$ hydrocarbon aryl, and wherein W is a substituent that enables linkage of the quinazoline to another quinazoline or quinoline of the invention, preferably via a sugar-phosphate backbone, and is most preferably selected from the group consisting of a halo, a 2'-deoxy-beta-D-ribofuranos-1-yl, and a 5'-monophosphorylated-2'-deoxy-beta-D-ribofuranos-1-yl.

According to another aspect of the present invention, a substituted quinoline is provided which has the following formula:

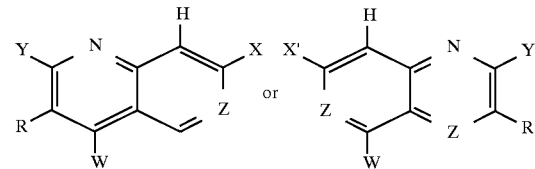

wherein X is selected from the group of $H,CO_2^-$, $CS_2^-$ and $SO_3^-$; Y is selected from the group consisting of NRR', OR, SRR', OR, and SR; R and R' are the same or different and are selected from the group consisting of hydrogen, lower alkyl, carboxyl and $C_6$–$C_{12}$ hydrocarbon aryl; Z is C—R; and wherein W is a substituent that enables linkage of the quinazoline to another quinazoline or quinoline of the invention, preferably via a sugar-phosphate backbone, and is most preferably selected from the group consisting of a halo, a 2'-deoxy-beta-D-ribofuranos-1-yl; and a 5'-monophosphorylated-2'-deoxy-beta-D-ribofuranos-1-yl.

The monomeric quinoline- or quinazoline-based compounds of the present invention are herein referred to as "anti-GC", "anti-CG", "anti-AT" and "anti-TA", based on which of the interstrand nucleotide base pairs in duplex Watson-Crick DNA molecules each specifically recognizes for binding. Exemplary of the novel monomers of this invention are the compounds represented by the formulas set forth in FIG. 4 which are denominated "anti-AT", "anti-TA", "anti-GC" and "anti-CG". In the exemplary quinazoline compounds, anti-AT and anti-TA, the following substituents are preferred.

X is —$NH_2$, —OH, —SH or —NHCOR;
Y is —H, —$NH_2$, —OH, —SH or —NHCOR;
Z is —CH;
R is —H, -alkyl or -aryl; and
W is halogen or deoxyribose.

The exemplary quinoline compounds of FIG. 4, anti-GC and anti-CG, comprise the following preferable substituents:

X is —H, —$CO_2^-$, —$CS_2^-$, or —$SO_3^-$;
Y is —$NH_2$, —OH, —SH, or —NHCOR;
Z is —CH, or —N;
R is —H, alkyl, aryl, or nothing (when Z is —N); and
W is halogen or deoxyribose.

The "anti-bases" of this invention are herein referred to as TRIPSIDEs for the deoxyribose-substituted compounds, or TRIPTIDEs for deoxyribosephosphate compounds. The halogenated precursors are referred to as TRIPs. The term OLIGOTRIP is used to refer to an oligomeric TRIPTIDE that is designed to be the third strand in a triple helix motif, and wherein the TRIPTIDE units are generally linked through a sugar phosphate backbone, as described more fully hereinafter. This nomenclature is discussed more fully hereinafter.

Substitutions on the quinazoline or quinoline ring structures are designated by R, W, X and Y in FIG. 4. When W is a halogen group, the formulas depict novel TRIPs of the present invention. In general, the halogen of choice is chlorine, bromine or iodine.

Among possible substitutions on the ring structures at positions represented by R in FIG. 4 are included alkyls, generally having between about 1–10 carbons. Lower-alkyls are preferred; for example, methyl, ethyl, n-butyl, n-propyl, and their branched chain derivatives. R can also be an aryl, generally having between about 6–12 carbons and which can be substituted or unsubstituted. It is preferred that, when substituted, the substitutions be lower alkyls. In general, the only limitation on R and its substituted derivatives is that they must not interfere either in the capacity of the substituted TRIP to be linked into an oligomeric structure (an OLIGOTRIP), or in the capacity of the OLIGOTRIP to bind in the major groove of the targeted duplex DNA. Use of molecular modeling techniques in most cases will reveal whether a selected substituent will be effective or not.

In an especially preferred embodiment of this invention, the substituents represented by X and Y in FIG. 4 are —$NH_2$ —OH, or —SH or groups. (These groups can also be further substituted as described hereinafter.) These substituents appear to best satisfy the critical requirement that such substituents provide effective and appropriate hydrogen bond donor or acceptor atoms at precisely the correct position to optimize binding of the substituted monomeric compound to the appropriate and complementary nucleotide base pair in the targeted DNA double helix. The concept of acceptor and donor atoms in the formation of hydrogen bonds is shown in FIG. 3, where the open arrows containing the letter "A" indicate the hydrogen bond acceptor atoms, and the open arrows containing the letter "D" indicate the hydrogen bond donor atoms.

The TRIPs of the this invention are useful as intermediates for the synthesis of the TRIPSIDES of this invention. The latter are depicted in FIG. 4 when W is a deoxyribose moiety (e.g., a 2'-deoxy-beta-D-ribofuranos-1-yl). These TRIPSIDES are precursors for synthesizing the novel oligomeric OLIGOTRIPs of the present invention and constitute the repeating units of such OLIGOTRIPs when appropriately linked through suitable sugar backbones as discussed more fully hereinafter.

Referring again to the nomenclature used herein, in general, the quinazoline compositions of this invention are "anti-AT" or "anti-TA", and the quinoline compositions are "anti-GC" or "anti-CG". When these compounds are halogenated at the 4-position or the 5-position, they are herein referred to as TRIPs. When the halogen is replaced with a linking substituent, such as ribose, deoxyribose or amino acid units (e.g., N-(2-aminoethyl)glycine), the compounds are herein referred to as TRIPSIDES, consistent with standard nucleotide nomenclature. The phosphorylated derivatives of the present invention are herein referred to as TRIPTIDEs. Furthermore, the TRIPTIDE is herein used when reference is made in the following discussion to the substituted quinoline- or quinazoline-bases when they are already part of an oligomeric structure. The term OLIGOTRIP is used herein to refer to a polymer comprising TRIPTIDE repeating units. According to the present invention, an OLIGOTRIP is designed to be the third strand in a triple helix motif. All other standard nucleotide nomenclature is believed to have been maintained.

The unique oligomers of this invention have clear advantages over traditional triple helix motifs. One significant advantage is that heterogeneous (mixed) sequences of purines and pyrimidines in the duplex DNA molecules can now be targeted in forming a triple helix structure; the traditionally-limiting requirement of targeting only homopurine/homopyrimidine nucleotide sequences is now eliminated. Another clear advantage of the OLIGOTRIPs of the present invention is that protonation of cytosine (C), which is essential in forming stable traditional $C^+$-G—C triplex complexes using the pyrimidine motif, is no longer required. Furthermore, the OLIGOTRIPs herein described are designed to effectively utilize the major-groove hydrogen-bonding information associated with purine and, optionally, pyrimidine bases in the targeted DNA molecule. This feature eliminates the constraint of homopurine stretches heretofore required for formation of triple helix motifs. As a result, the OLIGOTRIPs of this invention form very stable sequence-specific triple helix structures which lie with their sugar-phosphate backbone near the center of the major groove of the targeted double-stranded DNA molecule.

The following embodiments are illustrative of four groups of TRIP and TRIPSIDE bases of this invention:

Anti-AT TRIPS and Anti-AT TRIPSIDEs:

These are substituted monomeric quinazoline-based compounds which are capable, when incorporated into an oligomer of such monomers, of complementary binding to an adenine→thymine (A—T) interstrand base pair in a DNA double helix. The formula in FIG. 4, designated "anti-AT", is exemplary of such "anti-AT" TRIP compounds, when W is a halogen group. It is exemplary of an "anti-AT" TRIPSIDE when W is a deoxyribose sugar group.

Anti-GC TRIPs and Anti-GC TRIPSIDEs:

Falling within this group are substituted monomeric quinoline-based compounds which are capable, when incorporated into an oligomer of such monomers, of specific binding to a guanine→cytosine (G—C) interstrand base pair in a DNA double helix. The formula in FIG. 4 which is designated "anti-GC" is exemplary of an "anti-GC" TRIP compound when W is a halogen group. It is exemplary of an "anti-GC" TRIPSIDE when W is a deoxyribose sugar group.
Anti-TA TRIPs and Anti-TA TRIPSIDEs"

Substituted monomeric quinazoline-based compounds which are capable, when incorporated into an oligomer of such monomers, of specific binding to a thymine→adenine (T—A) interstrand base pair in a DNA double helix fall in this group. The formula in FIG. 4 which is designated "anti-TA" is exemplary of an "anti-TA" TRIP compound when W is a halogen group. It is exemplary of an "anti-TA" TRIPSIDE when W is a deoxyribose sugar group.
Anti-CG TRIPS and Anti-CG TRIPSIDEs:

This group includes substituted monomeric quinoline-based compounds which are capable, when incorporated into an oligomer of such monomers, of specific binding to a cytosine→guanine (C—G) interstrand base pair in a DNA double helix. The formula in FIG. 4 which is designated "anti-CG" is exemplary of an "anti-CG" TRIP compound when W is a halogen group. It is exemplary of an "anti-CG" TRIPSIDE when W is a deoxyribose sugar group.

Thus, each monomeric TRIP compound of this invention, when converted to its corresponding TRIPTIDE and incorporated via synthetic pathways described more fully hereinafter, into a polymeric OLIGOTRIP molecule, is designed to bind specifically to only one type of interstrand nucleotide base pair in a double-stranded DNA helix. As a consequence, the synthetic oligomeric OLIGOTRIPs of the present invention have the capacity to associate by hydrogen bonding with sequence specificity, via a stable triple helix motif, to targeted nucleotide sequences in duplex Watson-Crick DNA. Because each TRIP monomer (and its corresponding TRIPSIDE and TRIPTIDE monomers) associates by hydrogen bonding to the purine partner or to both the purine and the pyrimidine molecules in an interstrand base pair in a targeted double-stranded DNA helix, both strands of the targeted duplex DNA molecule can thereby be involved in the binding strategy.

Illustrative of this concept is the following diagram, which shows a sequence of certain novel quinoline- and quinazoline-based compositions, each in the form of a preferred embodiment of the present invention and linked together by a sugar-phosphate backbone, running in the 3'-to-5' direction, with the targeted DNA strand on the viewer's left running in the 5'-to-3' direction, from top to bottom):

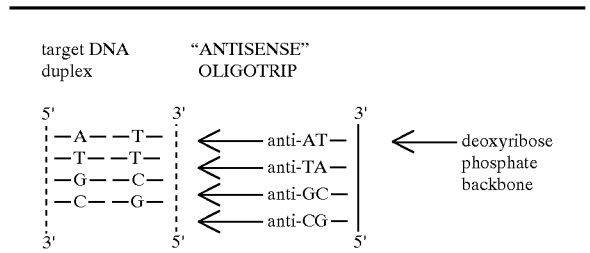

| wherein "anti-AT" is: | 2-amino-4-(2'-deoxy-beta-D-ribofuranos-1-yl)-7-hydroxyquinazoline; |
| --- | --- |
| "anti-TA" is: | 2-amino-5-(2'-deoxy-beta-D-ribofuranos-1-yl)-7-hydrozyquinazoline; |
| "anti-GC" is: | 2-amino-4(2'-deoxy-beta-D-ribofuranos-1-yl)-7- |

-continued

| "anti-CG" is: | carboxyquinoline; 2-amino-5-(2'deoxy-beta-D-ribofuranos-1-yl) -7-carboxyquinoline. |
| --- | --- |

In these chemical descriptions, the "-yl" term refers to the position of sugar attachment to the TRIP moiety, and the TRIPTIDEs are connected by a conventional phosphate linkage.

The novel compounds of the present invention are designed to bind near the center of the major groove by recognizing major groove hydrogen bonding information and by virtue of a unique backbone conformation, thereby eliminating the severe limitations of the traditional homopurine and homopyrimidine triple helix motif.

The structure of certain preferred embodiments of the novel quinoline- and quinazoline-based compositions of the present invention are shown in FIGURE 5. Where W is a halogen group, the structures in the FIGURE represent an especially preferred embodiment of the TRIP bases of the present invention. Where W is a deoxyribose sugar moiety, the structures in this FIGURE represent an especially preferred embodiment of the TRIPSIDEs of the present invention. Also shown in this FIGURE is the relative spacial positioning of each novel base an its targeted interstrand nucleotide pair.

BRIEF DESCRIPTION OF THE DRAWINGS

FIGS. 5A, 5B, 5C-1, and 5C-2 show the structure of certain preferred embodiments of the novel quinoline- and quinazoline-based compositions of the present invention. FIG. 5A shows compositions designed to recognize all H-bond information in the major groove (purine and pyrimidine combined). FIG. 5B shows compositions of the invention that recognize only purine H-bond information in the major groove. FIGS. 5C-1 and 5C-2 show compositions of the invention and by comparing compositions recognizing only purine H-bond information in the major groove ("motif A") FIG. 5C-1 with compositions recognizing all major groove H-bonding information ("motif B") FIG. 5C-2.

FIG. 6 shows the precise spatial arrangement of anti-GC with targeted interstrand G—C nucleotide base pair in duplex DNA.

FIG. 7 shows the precise spatial arrangement of anti-CG with targeted interstrand C—G nucleotide base pair in duplex DNA.

FIG. 8 shows the precise spatial arrangement of anti-AT with targeted interstrand A—T nucleotide base pair in duplex DNA.

FIG. 9 shows the precise spatial arrangement of anti-TA with targeted interstrand T—A nucleotide base pair in duplex DNA.

FIG. 12 demonstrates the pathway for synthesizing the novel TRIP of the present invention, 4-chloro-anti-AT.

DETAILED DESCRIPTION OF THE INVENTION

The TRIP bases of the present invention may be synthesized in two general motifs. In one motif, the bases are designed to recognize H-bond information contributed by purines in the major groove of duplex DNA. This motif is sometimes referred to herein as "motif A." In another embodiment, the bases are designed to recognize both purine- and pyrimidine-contributed H-bond information in the major groove. This embodiment is sometimes referred to herein as "motif B." The general description set forth in the paragraphs below apply to either motif A or motif B.

Additionally, although the TRIPS of the present invention are exemplified by compounds connected via a sugar-phosphate backbone, persons skilled in the art will understand that a variety of backbone structures known in the art (e.g., 5'-2' sugar phosphate linkages, peptide linkages) also may be used to produce the novel OLIGOTRIPS of the present invention.

A. Design of the third strand "synthetic monomeric bases".

1. The synthetic bases are planar aromatic bases. To ensure energetically favorable pi-stacking interactions required for stable helix formation, and to generate near "natural" helical twist angles, it is necessary that any synthetic base being newly designed for use in a synthetic oligomer be a planar aromatic system with at least one heteroatom. The term "heteroatom" as used in this context and hereinafter means an atom other than carbon. The significance of good stacking interactions cannot be underestimated in designing third strand bases (Manzini et al., J. Mol. Biol. 213: 833, 1990). The quinoline and quinazoline TRIPs of the present invention meet this criterion.

Figure 1:
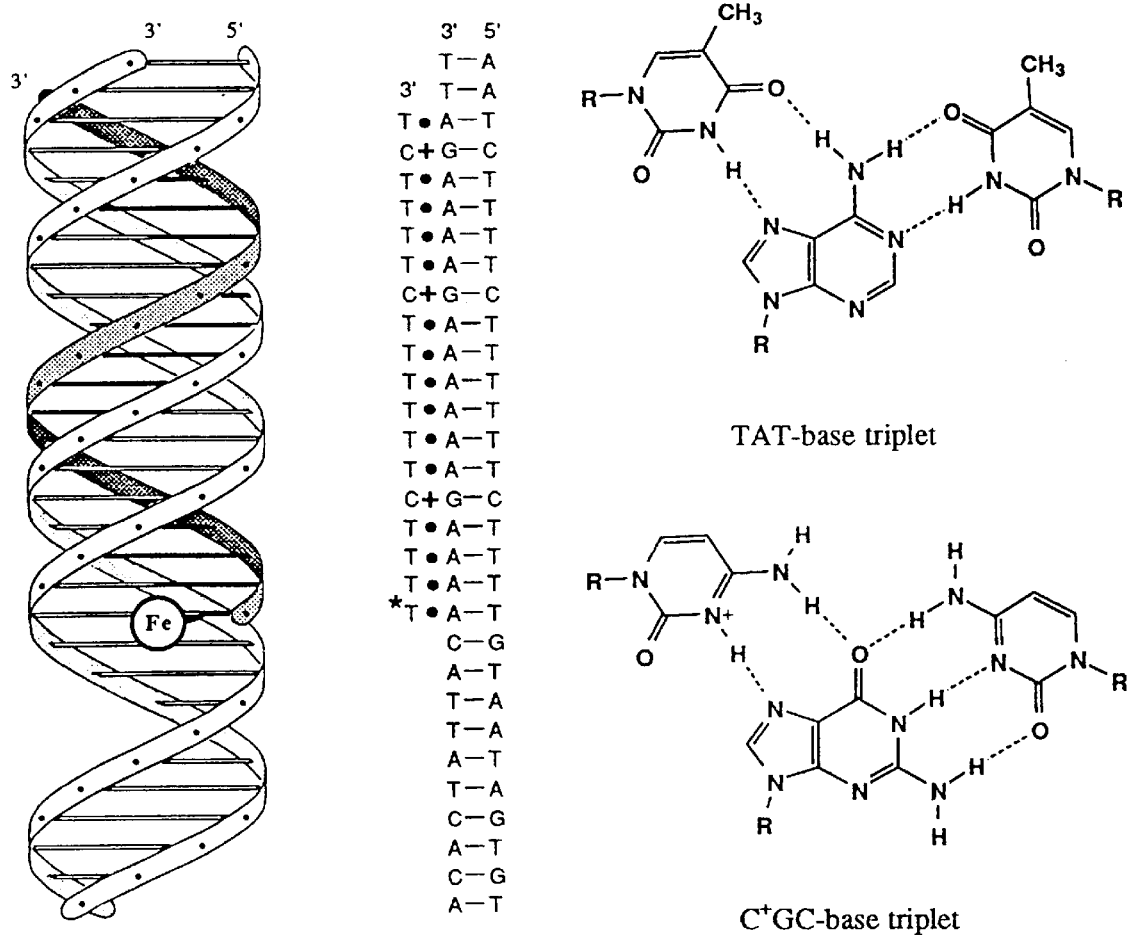
FIG. 1 shows traditional triple helix (Dervan picture) and Hoogsteen base pairing for $C^+$—G—C and T—A—T (reproduced from Strobel et al., J. Amer. Chem. Soc. 110: 7927, 1988). The double-stranded sequence is Sequence I.D. No.1; the triple helix-forming strand is Sequence I.D. No. 2.
Figure 2:
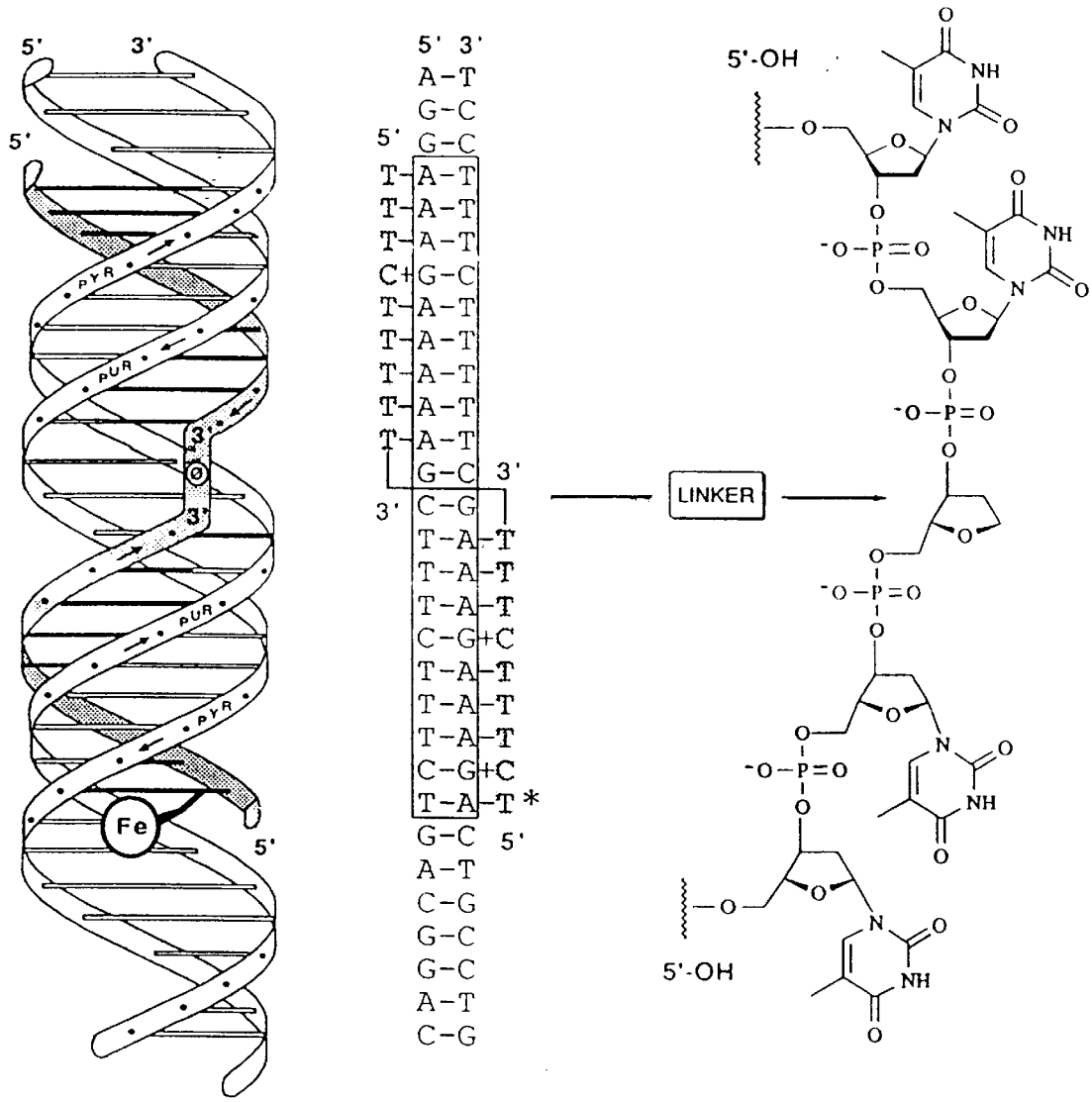
FIG. 2 diagrams how a purine-pyrimidine sequence requires part of the backbone of the third helical strand in the major groove to flip for A—T recognition on the two grooves (reproduced from Horne & Dervan, J. Amer. Chem Soc. 112: 2435, 1990) The double-stranded sequence is Sequence I.D. No. 3; the triple helix-forming strand is Sequence I.D. No. 4.
Figure 3:
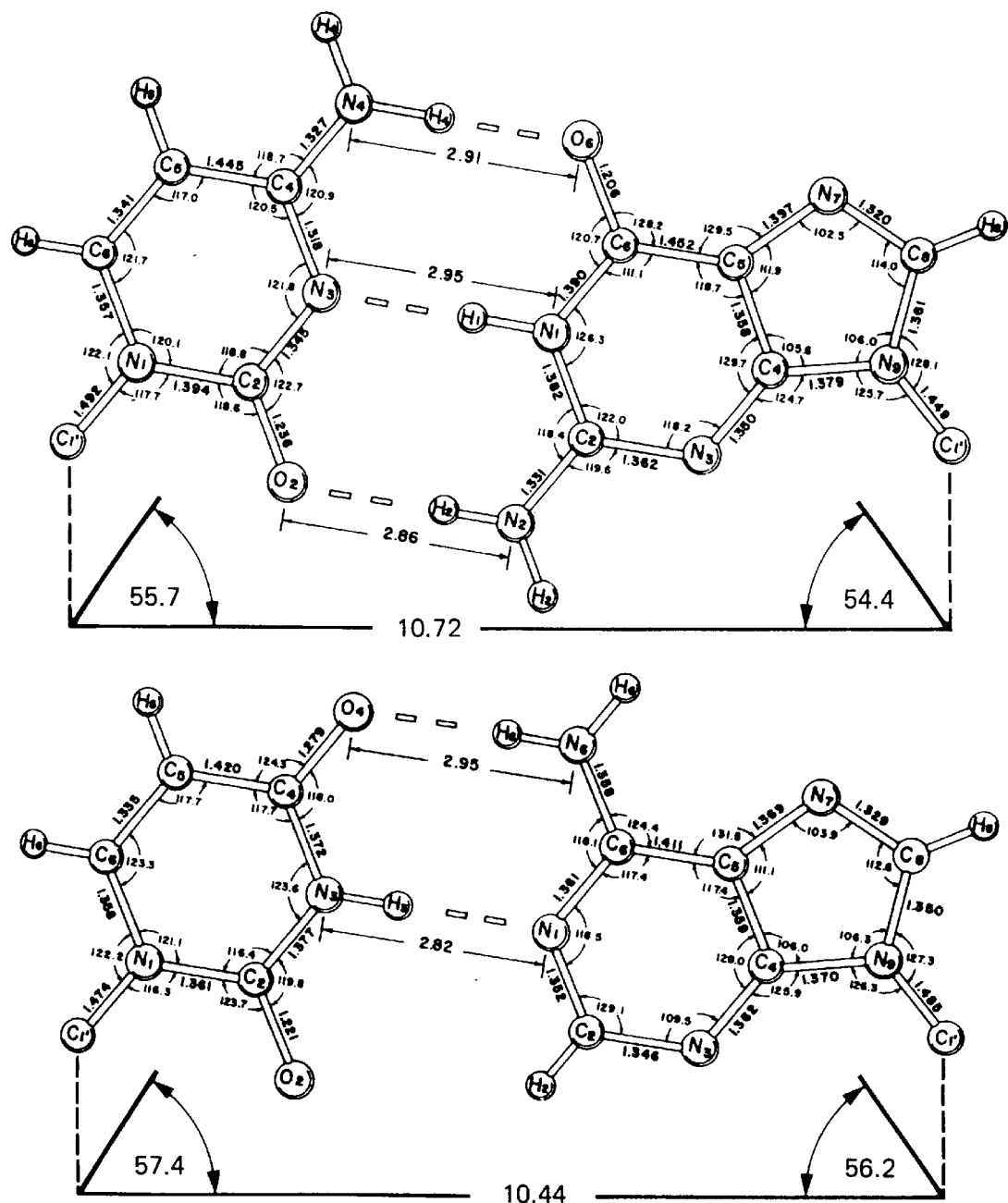
FIG. 3 shows the hydrogen bond donor and acceptor sites for G—C and A—U (equivalent to A—T) pairings as are available in the major groove of a duplex DNA molecule (modified from W. Saenger: *Principles of Nucleic Acid Structure*, Springer-Verlag, New York, 1984, p. 123).
Figure 4:
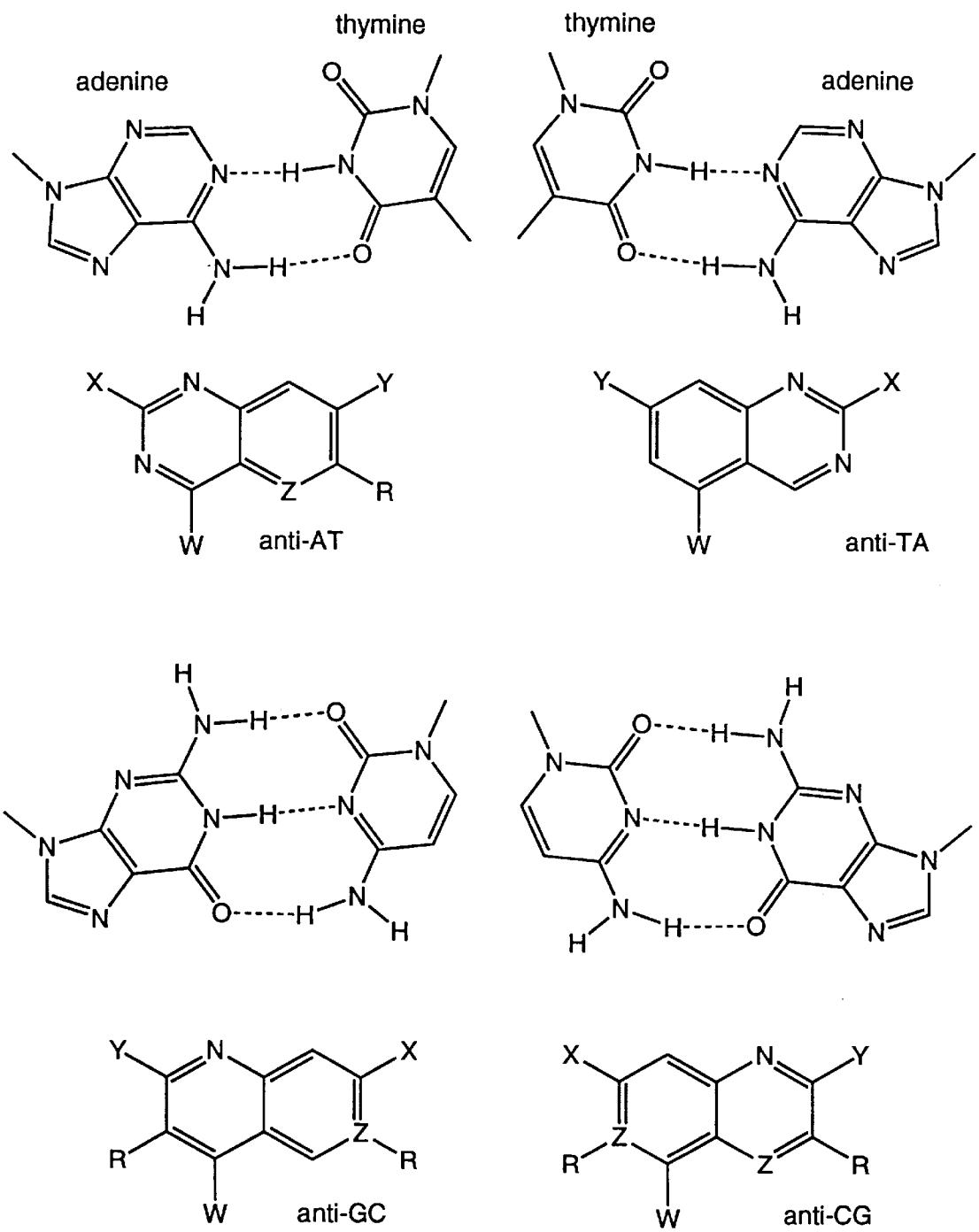
FIG. 4 shows where chemical substitutions may be made in the monomeric quinoline- and quinazoline-based compositions of the present invention.
Figure 5A:
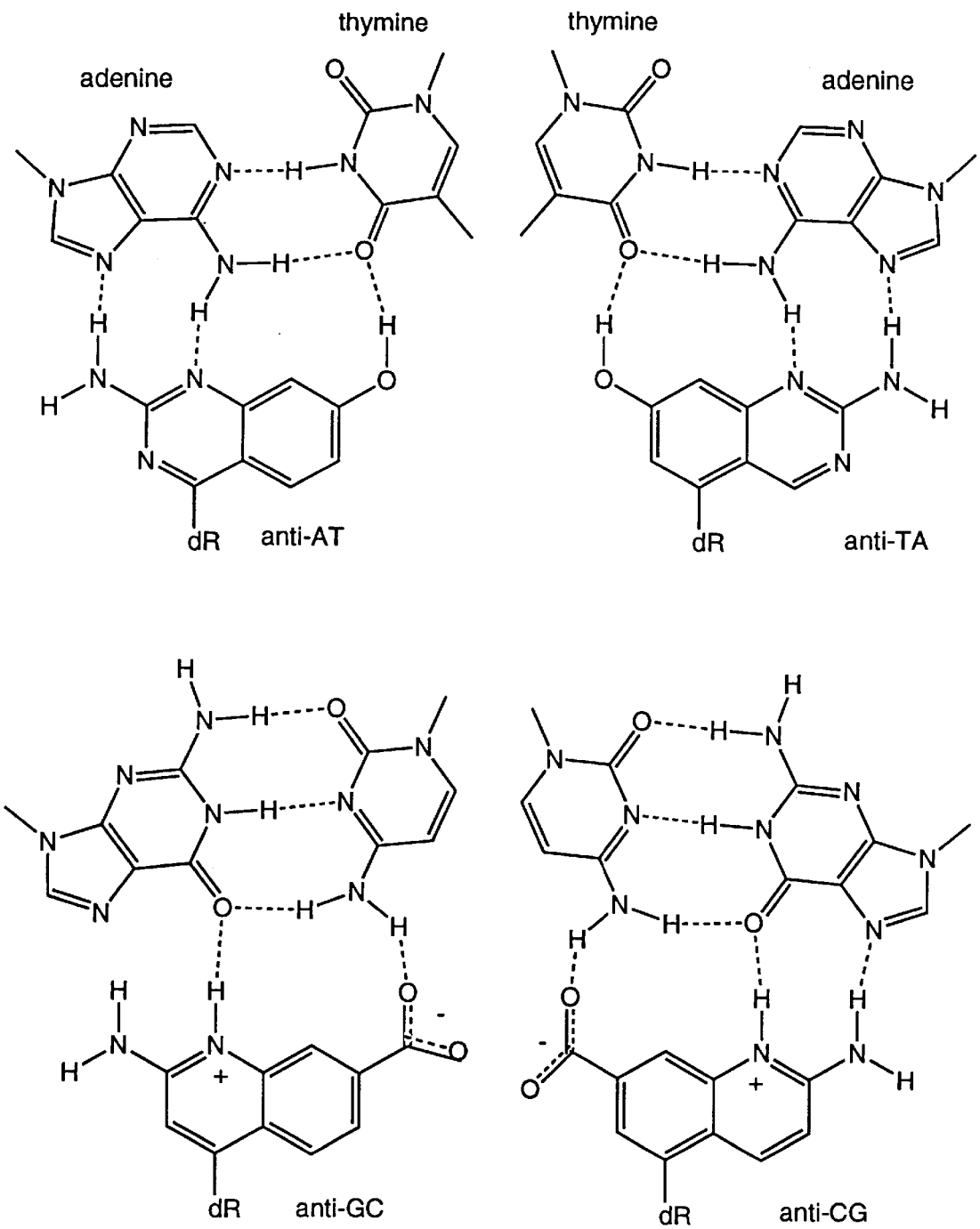
Figure 5B:
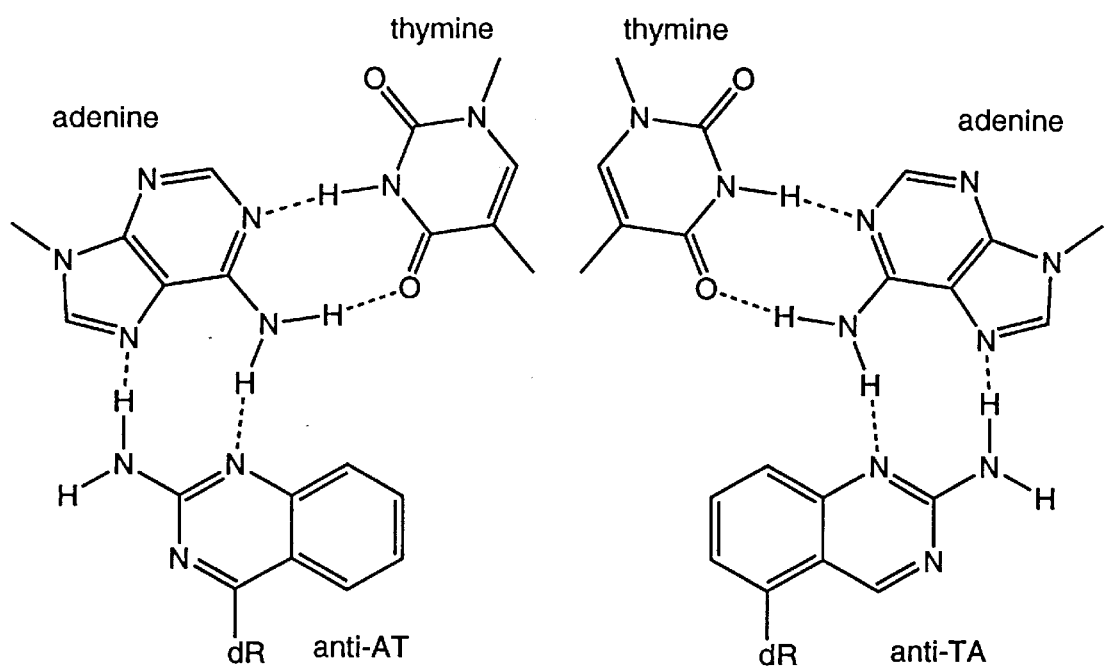
Figure 5B:
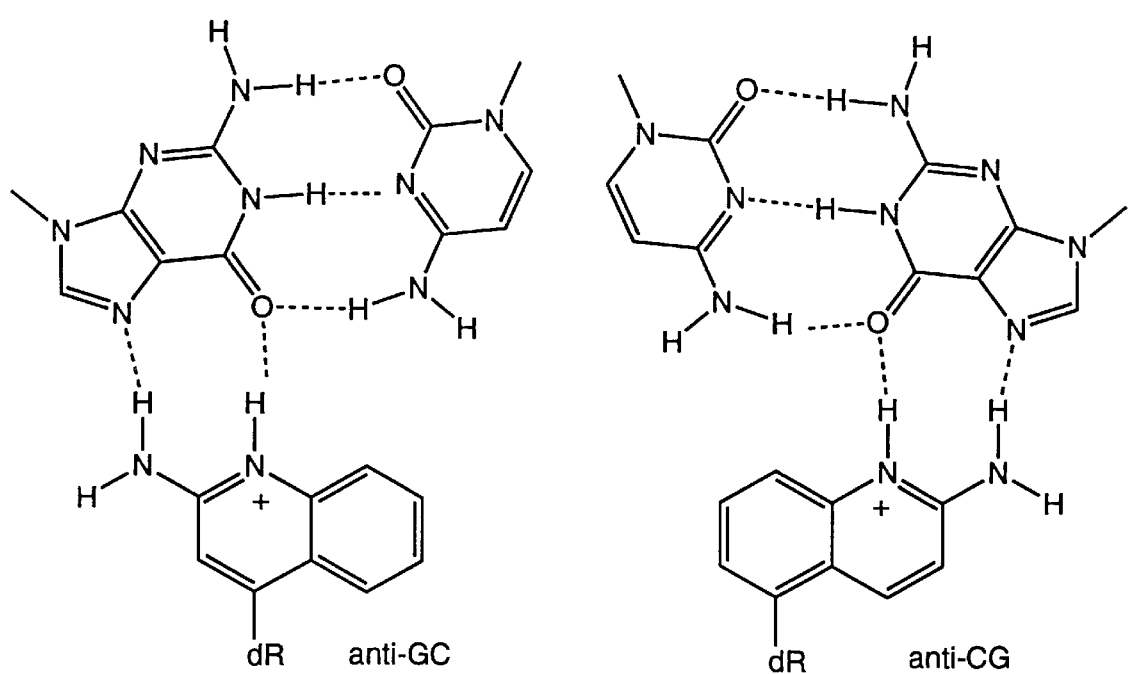
Figures 1, 5C:
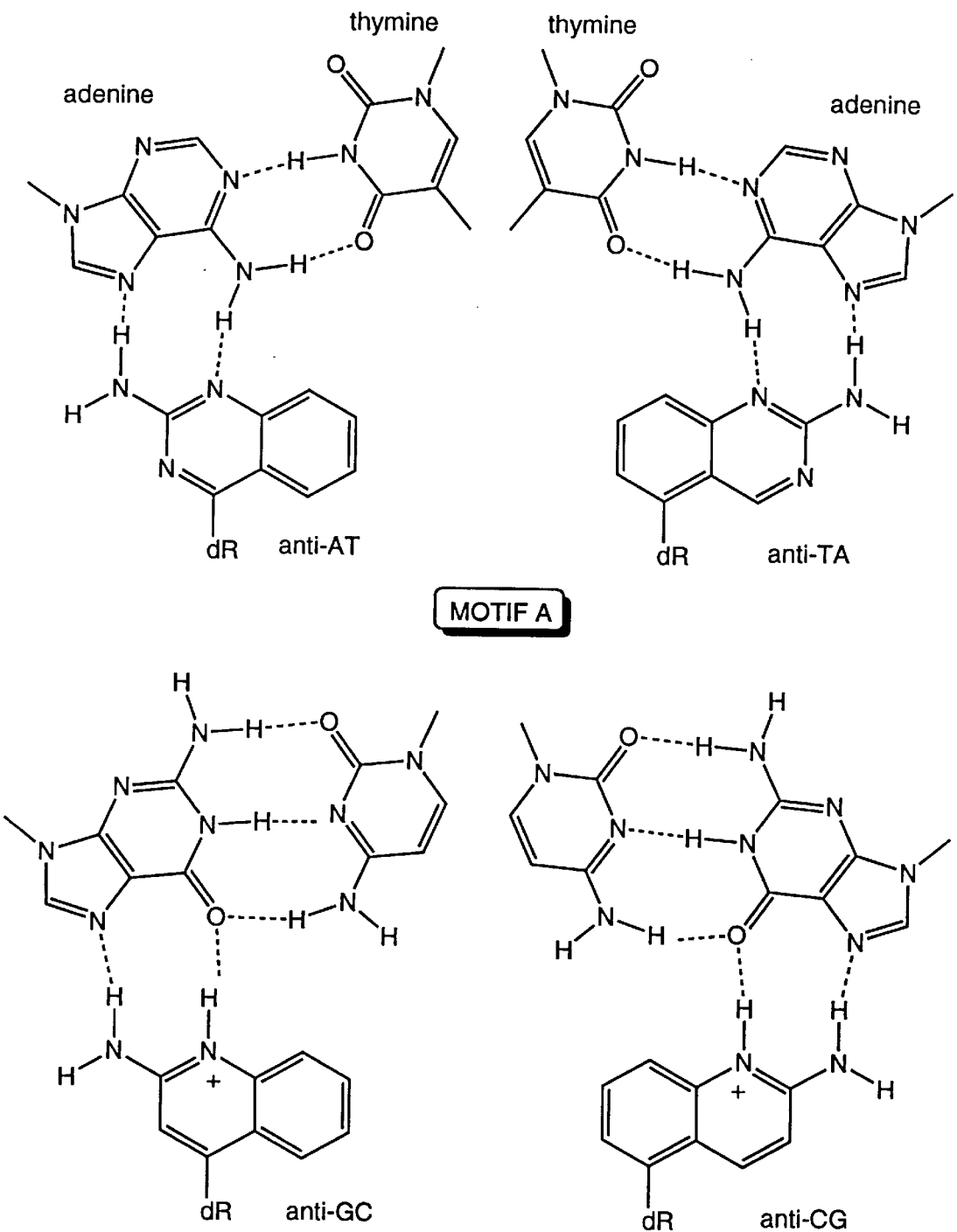
Figures 2, 5C:
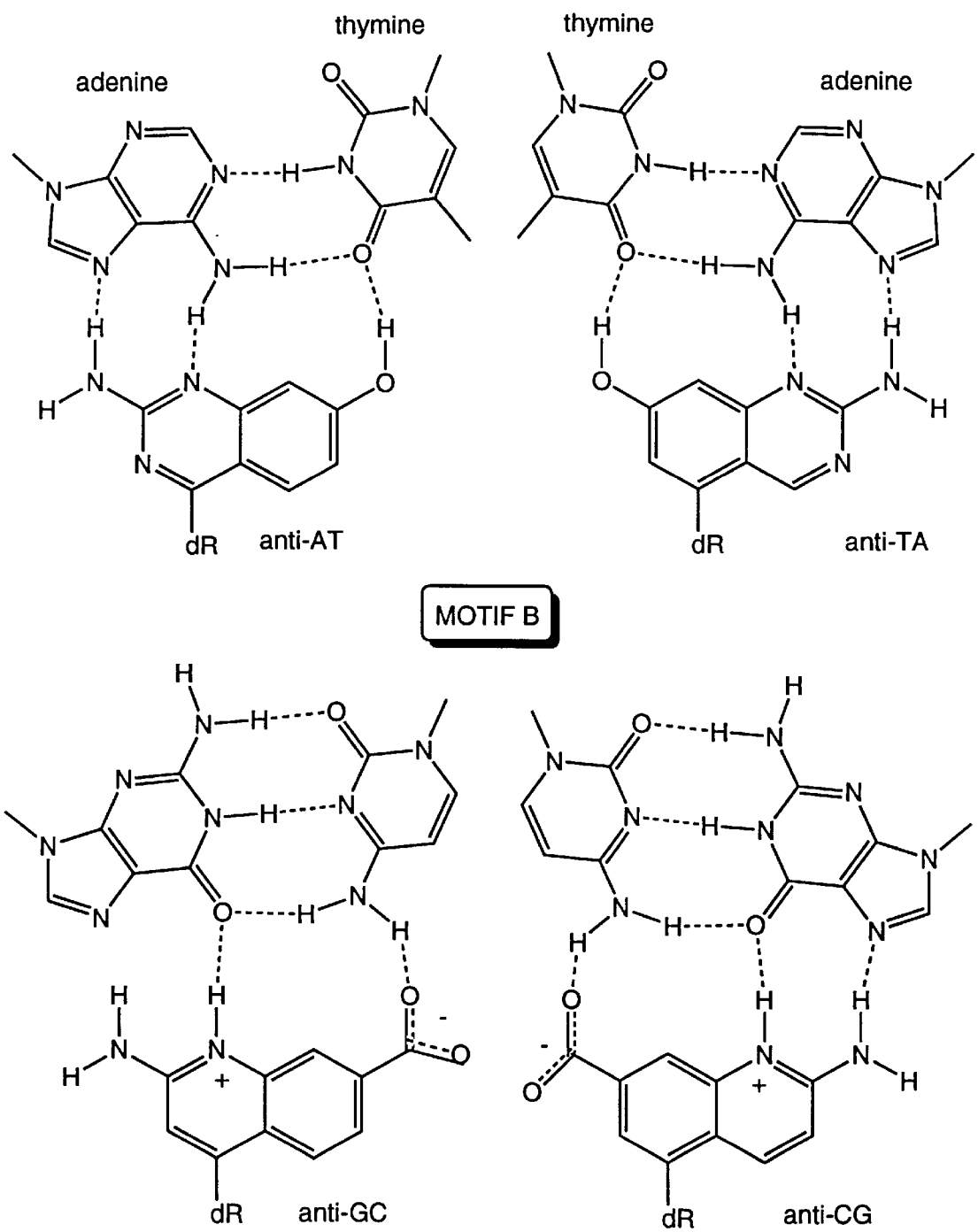
Figure 6:
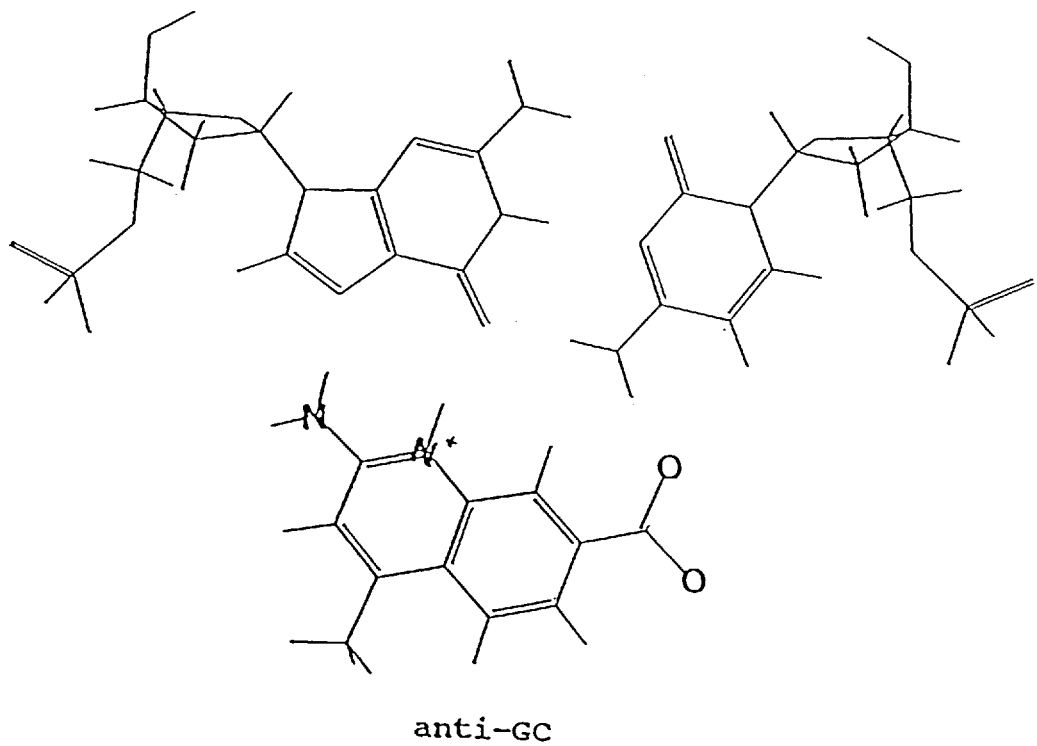
FIGS. 6, 7, 8 and 9 show computer-simulated three dimensional molecular modeling images of the precise spatial relationship of each of the different quinoline- and quinazoline-derived bases to the interstrand nucleotide pair to which it specifically binds in a targeted duplex DNA molecule.
Figure 7:
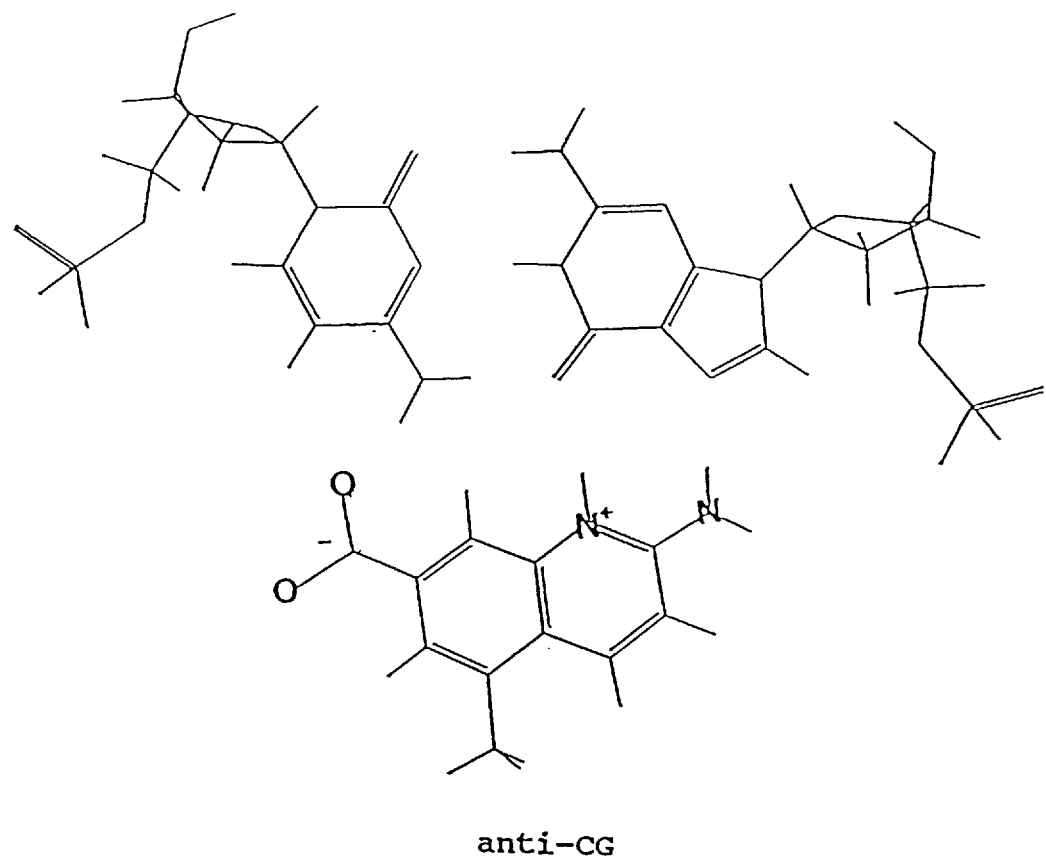
Figure 8:
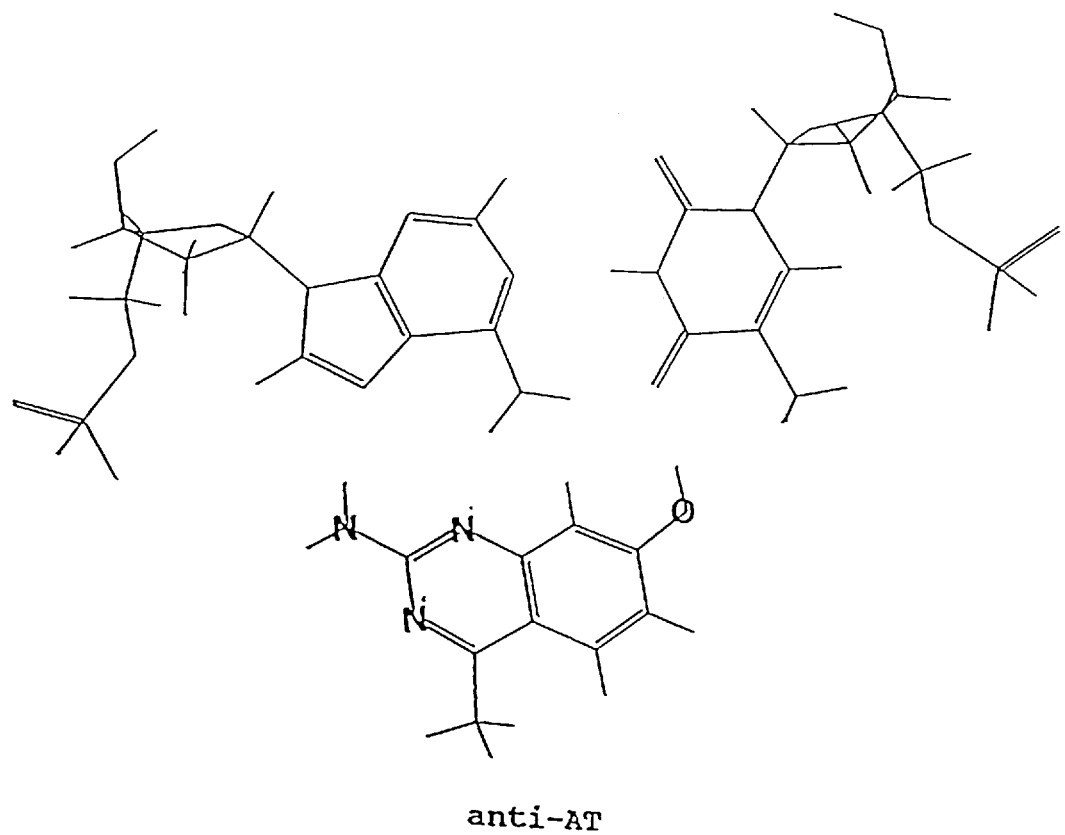
Figure 9:
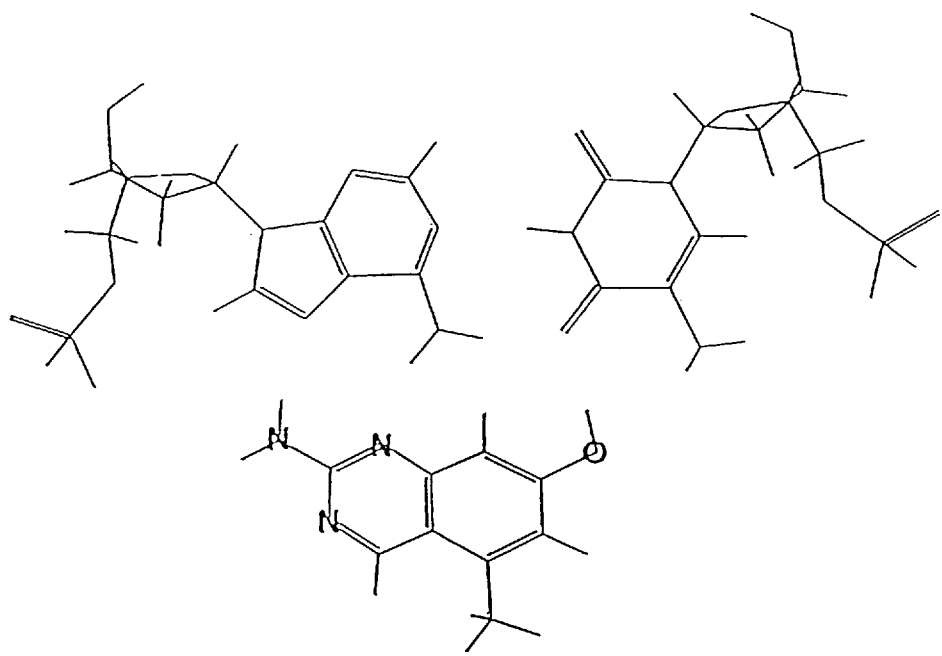

2. The synthetic bases recognize hydrogen bonding information in the major groove. The hydrogen bond donor and acceptor atoms located in the major groove are: N7-purine (acceptor), $O^4$-thymine (acceptor), $N^4H_2$-cytosine (donor), $N^6H_2$-adenine (donor) and $O^6$-guanine (acceptor) (FIG. 3). In all cases the geometrical center of the hydrogen bonding information is associated with the 6-position of the purine, although it is important to emphasize that this is not the center of the major groove. The distance from N7-purine to the exocyclic 4-position (oxygen or nitrogen) of the paired pyrimidine in Watson-Crick DNA is approximately six Angstroms in the B-form of DNA (B-DNA; see below) based on Dreiding molecular models and X-ray derived structures. There are two H's on both $N^4$-cytosine and $N^6$-adenine and only the hydrogen not involved in Watson-Crick base pairing is approached by a heteroatom acceptor with the proper orientation to afford a stable hydrogen bond (FIGS. 4 and 5). Note that the structures in FIGS. 4 and 5 are representative only, and are not precisely aligned (correct computer-generated spatial alignments are shown in FIGS. 6, 7, 8 and 9). The distance across the groove between the glycosidyl N's on the purine and pyrimidine is approximately 9.7 Angstroms. obviously groove dimensions are dependent on many factors related to sequence and the associated DNA conformations.

3. The synthetic bases differentiate between interstrand G—C and C—G bonding. The major groove hydrogen bonding information associated with an interstrand G—C (acceptor-acceptor-donor) base pairing (FIG. 3) and with an interstrand C—G (donor-acceptor-acceptor) base pairing differ; the third strand must be able to differentiate between these two pairing arrangements to afford high sequence specificity and to allow for reliable recognition of heteropurine/pyrimidine tracks. For interstrand C—G and G—C base pairs this is challenging because of the spatial relationship of the $N^4$-cytosine hydrogen that is not involved in Watson-Crick base pairing relative to the other atoms, coupled with the requirement that the hydrogen bonding atoms (N—H—X=C with X either nitrogen or oxygen) be relatively in line. The optimum angle for the three atoms is between 150°–177°, although smaller angles have been reported (Jeffrey & Takagi, Acc. Chem. Res. 11: 264, 1978).

The substituted quinoline-based compounds "anti-GC" (2-amino-7-carboxyquinolin-4-yl) and "anti-CG" (2-amino-7-carboxyquinolin-5-yl) of the present invention have pKa's that indicate that the carboxyl and the quinoline ring nitrogen are both ionized at neutral pH and form three hydrogen bonds with the proper orientation for bonding with interstrand G—C and C—G nucleotide base pairs in targeted DNA molecules. Anti-CG or anti-GC do not bind to interstrand A—T or T—A base pairs because the angular C-H of the quinoline ring system sterically blocks association with A—T or T—A pairings; the donor-acceptor arrangement also does not coincide with the hydrogen bonding atoms of the A—T or T—A pairings. The angular C—H does not sterically interact with the $O^6$-guanine position. The donor $N^4$-cytosine, and receptors $O^6$-guanine and N7-guanine make the necessary hydrogen bonds with the carboxylate anion, the protonated ring nitrogen and the exocyclic amino group.

The pKa of the ring nitrogen of 2-aminoquinoline is 7.3 and the 7-carboxy group has only a minor effect on the pKa. Therefore, the requirement for low pH to effect triple helical formation, as is required for the association of $C^+$—G—C in a traditional triplex structure, is not necessary with the novel OLIGOTRIPs of this invention. The angular C4-H (anti-CG) or C5-H (anti-GC) prevents rotations of the quinoline ring around the glycosidyl bond and fixes the TRIP in the anti-configuration with respect to the deoxyribose ring. The sugar connection to either the C-4 or C-5 position furnishes a carbon bond to the sugar that is perpendicular to the hydrogen bonding atoms of the monomeric TRIP and, therefore, provides the centrally located backbone that is necessary to accommodate mixed purine-pyrimidine runs.

4. The synthetic bases differentiate between interstrand T—A and A—T base pairings. As stated above, interstrand A—T and T—A base pairings at the simplest level are equivalent in terms of hydrogen bonding information. However, there is a subtle difference in the spatial relationship of the three hydrogen bonding atoms (receptor atoms of N7-adenine and $O^4$-thymine and the donor atom of $N^6H_2$) that is exploited in the present invention. This difference is depicted in FIGS. 4 and 5, which underscores two key points: 1) the steric interaction between the angular C8-<u>H</u> of the quinazoline ring system and the exocyclic $NH_2$ group of adenine; and 2) the requirement that the three atoms in a hydrogen bond interaction (X-H—Y) form an angle of 160°–178°. The novel anti-TA moiety of the present invention can form three hydrogen bonds only to an interstrand T—A base pair because the C8-H can only accommodate the correct base pair match. In fact, it does not form more than one reasonable hydrogen bond to the interstrand A—T pair. Similarly, the novel anti-AT moiety of the present invention specifically interacts with interstrand A—T only and not with T—A pairing. Neither of these compound have any steric interaction with the 5-methyl group of thymine.

The quinazoline ring system is especially useful in the present invention because of its angular C8-<u>H</u> which causes powerful steric interferences with the "wrong" duplex base pairs, and because the pKa of 2-aminoquinazoline is approximately 4.8; this means that the ring N-1 is not protonated. In contrast, 2-aminoquinoline has a pKa of approximately 4.9 for quinoline itself. The 7-hydroxyl substitution on the quinazoline ring system increases the pKa by 0.5 unit, as indicated by the 5.5 pKa of 7-hydroxyquinoline.

As discussed above for the novel anti-GC and anti-CG monomeric moieties of the present invention, steric constraints ensure that these bases adopt the "anti"-configuration around the glycosidyl bond. This makes the quinoline-4-yl- and -5-yl- substituted TRIPSIDEs quite different in their presentation to the DNA groove. The backbone connected to these positions at the C-4 or C-5 positions provides the centrally located backbone that is necessary to accommodate mixed purine-pyrimidine runs.

5. Exemplary synthetic bases are produced from syntheses compatible with phosphoramidite chemistry. To facilitate implementation of the novel DNA triplex strategy of the present invention, it is important that the prepared OLIGOTRIP oligomers recognize and bind to any duplex DNA sequence. Clearly, the wide use of solid support-based DNA synthesis employing mechanized phosphoramidite chemistry makes this method of oligomer production most attractive. In a preferred embodiment, the sugar-phosphate backbone structure of the oligomeric OLIGOTRIPs of the present invention is readily synthesized as either a phosphodiester or a phosphorothioate backbone.

6. The position of the backbone of the synthetic bases. As noted above, the formation of a stable triple helix in regions of the targeted DNA molecules containing heterogeneous (mixed) sequences of purines and pyrimidines is not possible when the third strand contains natural nucleotide base structures. This is because the binding position of the third strand containing these natural bases must move from a point approximately three Angstroms from the glycosidyl nitrogen atom near the backbone of one strand to a location the same distance from the backbone on the complement strand; such a positional shift cannot be accommodated by the structures of the natural nucleotide bases. Thus, to read a purine on the complement strand, the backbone of the third strand has to traverse a distance across the major groove that is almost six Angstroms more than is required in a homogeneous stretch of purines. This abrupt shift across the major groove is not possible with triplex strands containing the usual 5'-to-3' sugar-phosphate backbone.

The breakthrough tactic of the present invention eliminates the need for these molecular gymnastics. By recognizing hydrogen bonding information in the major groove, and by having the sugar-phosphate backbone perpendicular to the plane described by the hydrogen-bonding atoms of the novel TRIP moieties of the present invention, the center of hydrogen bonding information is placed at a position six Angstroms from the glycosyl nitrogen of the purine nucleotides in the base sequences being targeted in the major groove of the double-stranded DNA molecule. Therefore, in a targeted heterogeneous sequence of purines and pyrimidines, the third strand has to traverse only an additional 1.5 Angstroms across the major groove to accommodate the optimal bonding distances between purine and pyrimidine bases in the targeted sequence. This does not require any change in the normal backbone linkages of the third strand because changes in sugar pucker can slide the TRIPTIDE base approximately one Angstrom further into the groove.

Another way to ensure stable positioning of the backbone of the synthetic oligomer within the major groove is to utilize phosphoramidite monomers joined with 5'-to-2' linkages. Insertion of this backbone modification into the third strand, where required, allows the backbone to more easily accommodate the variations in optimal bonding distances required for pyrimidine-purine to purine-pyrimidine backbone crossovers or transitions.

Another backbone structure that can be utilized in the present invention is an amino acid linkage, such as N-(2-aminoethyl)glycine, to join the TRIP bases. This linkage has been used to produce DNA analogs (termed "PNA" that exhibit hybridization characteristics obeying Watson-Crick hydrogen bonding rules (Egholm et al., Nature 365: 566–568, 1993).

The intrastrand distances discussed above are based on a standard B-DNA structure, which has a uniform 35.90° helical twist per base pair, as well as a 3.32-Angstrom mean rise per base pair. The same is true for A-DNA, which is a more compact structural form of relatively unhydrated DNA. There is evidence indicating that the A-DNA conformation seems to be induced in triple helical structures. Supporting this are observations that, in most crystal-derived A-DNA structures, the helical twist at CG steps is unwound by approximately 100 relative to GC steps (Takusagawa, J. Biomolec. Struct. Dyn. 7: 795, 1990). Thus, it is clear that DNA is conformationally promiscuous and is "free" to adopt a multitude of structures depending on the free energy of the system (duplex DNA of A-DNA or B-DNA structures, third strand, ligands, salts, water, etc).

7. Use of intercalators linked to third strand as stabilizers. Additional stabilization of triple helical structures using an intercalating molecule linked to the end of the third strand has previously been required to show in vivo activity against an eight basepair homopurine/homopyrimidine sequence (Birg, et al., Nucleic Acids Res. 18: 2901, 1990). Although the length of duplex DNA which can be targeted using the OLIGOTRIPs of the present invention is longer than eight basepairs in length, and more stable because of up to three hydrogen bonds per base, the preparation of synthetic oligomer containing an intercalator is yet another embodiment of the present invention.

B. Third-strand OLIGOTRIPs as "antisense" oligomeric probes.

Synthetic strings of DNA nucleotide bases which are complementary to the "sense (information bearing) strand of nucleic acids have become widely recognized in recent years for their ability to inhibit the expression of specific genes. *Oligodeoxyribonucleotides: Antisense Inhibitors of Gene Expression*, (J. S. Cohen, Ed.) CRC Press, Boca Raton, Fla., 1989). "Antisense" oligonucleotides are traditionally single-stranded nucleic acids which, by hybridizing either to the complementary DNA nucleotide sequence in a target gene, or more commonly, to the messenger RNA (mRNA) transcribed from that gene, are able to reduce or abrogate the function of the targeted gene. In a similar manner, synthetic strings of the novel monomeric compositions of the present invention (OLIGOTRIPs) are designed to be complementary and to bind with a specific information-bearing sequence of paired nucleotide bases in a targeted double-stranded DNA helix. Because these sequence-specific, complementary OLIGOTRIPs target duplex (double-stranded) DNA rather than cell and tissue proteins, they have the potential to be drugs that are an order or so of magnitude more selective than traditional drugs, a factor which should very significantly reduce problems of unwanted side effects.

The current thinking in antisense oligonucleotide therapy is to utilize homologous DNA-based oligonucleotides as therapeutic agents; i.e., as agents whose nucleotide base sequence is complementary to all or part of the nucleotide sequence of a cellular or viral gene believed to be important in causing or regulating a disease process. Similarly, synthetic OLIGOTRIPs, utilizing the novel monomeric compositions of the present invention, can be targeted to selected gene sequences for the purpose of controlling the expression of the targeted gene and formation of its product.

The size of the synthetic oligomer, i.e., the number of bases in the OLIGOTRIP sequence, is an important consideration. In practice, the length (in base numbers) of a traditional therapeutic antisense oligonucleotide ranges from at least about 8 bases to as many as about 100 bases. Especially preferred are oligonucleotides with from about 14 to about 25 bases. The longer the antisense oligonucleotide, the higher is its affinity for a target sequence when it binds with exact complementarily. Similar considerations exist for the use of synthetic OLIGOTRIPs. Furthermore, the longer the OLIGOTRIP sequence being utilized, the more unique is the targeted sequence. However, these advantages are offset by the fact that longer oligomers are also more difficult and costly to prepare and more difficult to handle.

The region of the target DNA to which the selected OLIGOTRIP is designed to hybridize is an important variable that affects the practice of this invention. Several criteria are used herein to select the targeted region. These are: (i) thermal stability of the hybrid complex; (ii) secondary structure in the targeted DNA region; and (iii) the transcriptional activity of the targeted region (i.e., the targeted region must be transcriptionally active so that physical accessibility is guaranteed).

The OLIGOTRIPs of the present invention are also useful as research tools, i.e., for experimental modification of a target DNA sequence of interest. For example, OLIGOTRIPs may be used for targeted delivery of DNA alkylating agents for studying the effect of such agents on gene expression.

The impetus for designing targeted equilibrium binding DNA alkylating agents arises from the knowledge that, although the modification of DNA is the initial step in the mechanism of action for many mutagens, carcinogens and antineoplastic agents, there is currently no common theme to the structure of the adducts or the sites of DNA modification. For example, the powerful liver carcinogen, aflatoxin B, appears to selectively form an adduct at 7-G, and this DNA modification is thought to be responsible for its tumorigenicity. However, the same 7-G site is considered to be relatively unimportant in the induction of hepatic tumors by methylating and ethylating agents that react at a variety of positions on the DNA in addition to 7-G. The diversity and variation in product yields makes it difficult to dissect the importance and roles of individual DNA lesions in mutagenicity and/or cytotoxicity.

In order to understand the mechanism(s) of genotoxic carcinogens, and to design more effective DNA damaging anti-cancer agents, it important to differentiate between DNA adducts that are promutagenic and/or cytotoxic, versus innocuous. Accordingly, it is desirable to design alkylating compounds to generate DNA adducts with groove and/or sequence specificity in order to change the "normal" alkylation pattern of the compound, and to determine the effect of this pattern change on the in vivo toxicity, mutagenicity and mutation specificity of the compound on the target DNA. The OLIGOTRIPs of the present invention are capable of modification to incorporate various alkylating agents, and therefore should be of particular utility in target-specific delivery of these agents to a DNA sequence under investigation. A preferred method for appending an alkylating functionality on to an OLIGOTRIP is described in detail in Example 9.

C. OLIGOTRIPs in therapeutics for systemic administration.

In accordance with the present invention, there is provided a novel and unexpected method for killing or inhibiting the growth of cancer cells which carry certain genes known to be related to the tumorigenesis process. To illustrate, the gene that encodes the cancer-related p53 protein is a gene target of particular interest to research and clinical oncologists, as it is considered to occur more frequently among human cancers than does any other cancer-related gene yet identified. Accordingly, p53 is a preferred target of the novel compositions of this invention. A number of cancers known to carry this gene are, for example, leukemias, lymphomas, myeloma, breast cancer, gastrointestinal cancers, and small cell carcinoma of the lung.

The method of the present invention for killing or inhibiting the growth of cancer cells involves contacting cancer cells in vivo or in vitro with a cytotoxically-effective amount of an appropriate OLIGOTRIP or combination of OLIGOTRIPs, or pharmaceutically-effective analogs thereof. In a preferred embodiment, the OLIGOTRIP or combination of OLIGOTRIPs, or pharmaceutically-effective analogs thereof, have TRIP-based sequences complementary to a sequence of interstrand nucleotide base pairs in the DNA of the p53 gene present in the cancer cells.

The term "cytotoxically-effective amount", as used herein, means an administered amount of a therapeutic OLIGOTRIP preparation which is well below the cytotoxic endpoint of the OLIGOTRIP preparation, but which is sufficient to kill or inhibit the growth of target tumor cells containing the targeted gene, in preference to other cells which do not contain the targeted gene. Exemplary of such a targeted cancer-related gene is the gene encoding p53.

The present invention also provides novel methods for treating an individual whose cancer cells contain a certain gene (or genes) which are identified as being related to the process of tumor development. Exemplary of such a gene is the gene encoding the cancer-related p53 protein. The methods for treating an individual with cancer involves the use of antisense OLIGOTRIP therapies, in which a cytotoxically-effective amount of a preparation containing an anti-p53 antisense OLIGOTRIP, or combination of selected anti-p53 antisense OLIGOTRIPs, or one or more pharmaceutically-effective analogs thereof, is administered as specific drug therapy of cancers which carry the p53 gene. In a preferred embodiment of the present invention, the OLIGOTRIP preparation is administered systemically to the individual. Thus, there is provided a method for treating an individual having cancer comprising administering to the individual a sufficient amount of a preparation containing OLIGOTRIPs complementary to duplex DNA in a target gene to kill or inhibit the growth of the cancer cells present in the individual.

It is becoming common to provide cancer-bearing individuals with intensive (potentially lethal) radio- and/or chemotherapy to ablate their tumor burden, followed by rescue with an autologous bone marrow transplant. More recently, rescue with an autologous peripheral stem cell transplant has been performed. However, these transplant procedures will have long-term value only when the autologous transplant cell suspensions are completely free of contaminating tumor cells.

Accordingly, in another embodiment of the present invention, autologous bone marrow cells (or peripheral blood-derived stem cells) from an individual with cancer whose cancer cells contain a known oncogene or cancer-related gene (such as p53, for example) are treated ex vivo with specific antisense OLIGOTRIPs to the cancer-related gene in order to eliminate the cancer cells which may be contained in the bone marrow or stem cell transplant specimen. This is a specific improvement over the current procedures being used to deplete contaminating tumor cells from, for example, an autologous marrow or stem cell suspension. After malignant cell depletion, the treated autologous bone marrow cells (or peripheral blood-derived stem cells) are infused back into the patient who has, in the meanwhile, received appropriate surgical, radiation, immuno- and/or chemotherapy.

In the case of an autologous bone marrow transplantation, the method for removing contaminating cancerous cells from the marrow cell suspension is straightforward, and comprises the steps of (i) collecting an appropriate amount of bone marrow (preferably about 1500 cc from multiple points in the pelvic iliac crest, although as little as 500 cc and as much as 2000 cc can be used) from the individual who has the cancer, and isolating the nucleated cells from the bone marrow sample; (ii) contacting the nucleated bone marrow cells ex vivo (in culture) with a cytotoxically-effective amount of an antisense OLIGOTRIP which has a base sequence complementary to the duplex DNA of a target gene (such as, for example, the gene encoding p53) present in the cells of the cancer (this incubation takes from about 12 hours to about 7 days); and (iii) thereafter infusing the treated bone marrow cells back into the individual patient who donated the marrow.

Thus, one method for removing cancerous cells from bone marrow cells obtained from an individual who has cancer involves the steps of:

a. collecting bone marrow cells from the having a cancer;
b. contacting the bone marrow cells ex vivo with a cytotoxically effective amount of an OLIGOTRIP, or combination of OLIGOTRIPs, which has a base sequence complementary to the duplex DNA of a cancer-related target gene also present in the cells of the cancer;
c. thereafter infusing the treated autologous bone marrow cells back into the individual at a clinically appropriate time.

In a particular embodiment of the present invention, the OLIGOTRIP used in treating the bone marrow cells is an anti-p53 OLIGOTRIP.

This form of intensive therapy can be further improved by the additional step of administering systemically to the individual, after the bone marrow transplant has engrafted, a therapeutic preparation of this invention containing anti-p53 antisense OLIGOTRIP, administered in an amount sufficient to kill or inhibit the growth of the few p53-positive cancerous cells which may remain in the individual.

The anti-p53 antisense OLIGOTRIPs of the present invention can be of significant clinical utility when administered systemically to individuals who have p53-positive cancers, concomitant with or following primary tumor ablation with surgery, radiation and/or chemotherapy. Additional therapeutic gains can be obtained by systematic administration of anti-p53 antisense OLIGOTRIPs to recipients of autologous bone marrow cell suspensions, after the bone marrow, itself purged of contaminating p53-positive cancer cells by treatment with anti-p53 OLIGOTRIPs, has engrafted in the individual.

For effective therapeutic utilization of the novel concepts of the present invention, the anti-p53 antisense OLIGOTRIPs are administered in vivo as a systemic therapy, and they can also be administered in vitro, as a procedure for eliminating contaminating p53-positive tumor cells from a suspension of autologous peripheral blood stem cells or autologous bone marrow cells. Depending on the intended utilization, the physical form of the therapeutic preparation may vary, as discussed more fully hereinafter.

1. Nuclease-resistant backbone structure is the preferred embodiment of the present invention. For an "antisense" OLIGOTRIP to be useful as a therapeutic agent following systemic administration, it must survive in solution long enough to reach its designated target gene in the body and block the activity of that target gene. To survive in vivo long enough to be effective therapeutically, the OLIGOTRIP must be resistant to nucleases.

The "normal" structure of an OLIGOTRIP is a defined sequence of novel TRIPTIDE bases built upon a sugar-phosphate backbone containing phosphodiester linkages. There is substantial evidence that these phosphodiester linkages are highly susceptible to rapid degradation by a variety of nucleases found in abundance in tissues and cellular fluids. However, attachment of the modified monomeric structures of the present invention to a phosphodiester backbone results in nuclease resistance. OLIGOTRIPs, therefore, do not require a phosphorothioate backbone in order to have nuclease resistance.

Known nuclease-resistant backbone linkage structures can also be employed in the OLIGOTRIPs of this invention. A number of such linkage structures are known in the art to be nuclease resistant (for example, see the discussion of nuclease-resistant linkages in Stein et al., Nucleic Acids Research 16: 3209–3221, 1988). One such linkage is the phosphorothioate linkage. Phosphorothioates are compounds well known in the art, in which one of the non-bridging oxygen atoms in the phosphate portion of a nucleotide is replaced by sulfur. The use of OLIGOTRIP analogs which contain a backbone of phosphorotioate linkages is based on the known resistance of this interbase linkage to degradation by nucleases of many types when used to link the natural nucleotide bases found in DNA or RNA. Since phosphorothioates also have the same number of charges as normal phosphodiester-linked oligomers, they have good aqueous solubility.

The conventional nuclease-resistant phosphorothioate backbone linkage does not diminish the potential for sequence specific recognition by the OLIGOTRIP analog for its target gene. Furthermore, it is anticipated that, because of the "abnormal" quinoline and quinazoline bases and the C-glycoside linkage, the OLIGOTRIP would be more stable than DNA.

In addition to the preferred phosphorothioate linkage, the "antisense" OLIGOTRIPs selected for practice of the present invention may have nuclease-resistant ethyl- or methylphosphonate linkages between the novel TRIPTIDE bases. OLIGOTRIP analogs with these types of linkages may be less efficient at hybridization with a complementary DNA sequence than are the corresponding analogs which incorporate phorphorothioate linkages. On the other hand, OLGIOTRIPs having a methylphosphonate backbone are more lipophilic than are the other analogs, and this may prove advantageous in certain circumstances.

To those skilled in the art, it is known that nuclease-resistant backbone linkages other than those mentioned above are readily available for incorporation into all or part of a newly-synthesized OLIGOTRIP. Furthermore, it is also known that other nuclease-resisting linkages are continually being developed. It is the intent of the present invention to include within its scope any "antisense" OLIGOTRIP used alone or in combination with other therapies, and which contains such nuclease-resistant backbone linkages.

2. Use of antisense OLIGOTRIPs in pharmaceutical formulations. For systemic administration to a mammalian host, the therapeutic "antisense" OLIGOTRIPs of the present invention can be formulated into a variety of pharmaceutical compositions, depending upon the protocol to be used for systemic administration. In general, the pharmaceutical compositions employ a therapeutically effective amount of the OLIGOTRIP in a dosage and form sufficient to carry out the purpose of the formulation without causing unacceptable toxicity for the patient, i.e., a "pharmaceutically acceptable and effective amount" of the OLIGOTRIP. The therapeutic amount which represents an optimal therapeutically-effective dose for treatment of a particular clinical problem can be determined empirically by the chemotherapist. In general it will be the minimal dose which is sufficient to achieve an effective blood concentration of OLIGOTRIP and, generally, will fall within the range of from about 0.1 to about 200 micromolar.

The "antisense" OLIGOTRIP compounds of the present invention (also referred to hereinafter as the "active ingredients" or "active compounds"), in whatever analog prepared, are administered in a variety of dosage forms. In addition to the active ingredient, any of a number of pharmaceutically-acceptable excipients which facilitate formulation of the active ingredient into suitable dosage form can be used. In a preferred embodiment, the preparations are designed for parenteral administration. However, pharmaceutical compositions designed for oral administration in such forms as tablets, capsules, and dragees, or for rectal administration in the form of suppositories, are also considered to fall within the scope of the present invention.

Appropriate formulations of a therapeutic OLIGOTRIP for parenteral administration include aqueous solutions of the active compound prepared in a water-soluble or water-dispersible form. Alternatively, the active compounds are administered as suspensions in appropriate oily injection carriers, i.e., in suitable lipophilic carriers, such as fatty oils (sesame oil being an example), or synthetic fatty acid esters (ethyl oleate or triglycerides being examples). Pharmaceutical formulations prepared for aqueous injection may contain substances which increase the viscosity of the suspension such as, for example, sodium carboxymethyl cellulose, sorbitol, and/or dextran.

The therapeutic "antisense" OLIGOTRIPs of the present invention may also be administered encapsulated in liposomes. In such pharmaceutical preparations, the "antisense" OLIGOTRIPs are contained in corpuscles which consist of concentric aqueous layers interspersed between hydrophobic lipidic layers. The OLIGOTRIPs, depending upon their solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as a diacetylphosphate, stearylamine, or phosphatidic acid, and/or other materials of a hydrophobic nature which are generally well known in the art.

3. Antisense OLIGOTRIP treatment of bone-marrow cells.

Purging bone marrow suspensions of contaminating tumor cells is presently accomplished either by in vitro incubation of the transplanted marrow cells with potent anti-cancer chemotherapeutic agents, or by contacting the bone marrow cells with immunotherapeutic agents which recognize certain structures unique to the surface membrane of tumor cells.

A major difficulty with immunotherapy is that many tumor cells fail to express the tumor-associated membrane structure, and thereby go unrecognized by the immunotherapeutic agent. On other tumor cells, the immunotherapeutic agent binds to its target but fails to kill the cell. With regard to chemotherapeutic agents, most of the agents are highly toxic and must be used at relatively high dose in order to maximize tumor cell kill. However, this can lead to death of a large number of normal marrow cells and, in some instances, to graft failure. What is needed, therefore, is a bone marrow purging agent which selectively attacks tumor cells and leaves the normal marrow cells intact. The present invention provides such a novel agent for use with cancers of a variety of types. Exemplary are those cancers which are p53-positive cancers.

Thus, in another embodiment of the present invention, anti-p53 antisense OLIGOTRIPs are used to remove p53-positive cancer cells obtained from the afflicted individual. In this latter technique, bone marrow cells are obtained from an individual who has a p53-positive cancer, using standard procedures, which include aspiration from the pelvic iliac crest of a donor, as described, for example, in U.S. Pat. Nos. 4,481,946 and 4,486,188. The patient from whom the bone marrow has been taken is then treated with radiation or chemotherapy to destroy the p53-positive cancer cells which are in one or more organs of the body. Because this intensive therapy also destroys sensitive stem cells required for reestablishment and regrowth of such vital systems as the hematopoietic system, the treated patient must be replenished with healthy autologous bone marrow cells. Clearly, it is to the long-term advantage of the patient if the bone marrow cells returned to the patient are entirely free of cancer cells. These and other potential concerns are discussed in detail in: *Autologous Bone Marrow Transplantation: Proceedings of the Third International Symposium*, K. Dicke (Editor), The University of Texas M. D. Anderson Hospital and Tumor Institute at Houston, 1987.

The sample of autologous bone marrow cells is then immediately treated with the anti-p53 OLIGOTRIP, as discussed below, and reinfused into the donor as soon as is appropriate. In such a treatment, the autologous bone marrow is purged of contaminating p53-positive cancer cells by exposure ex vivo to a cytotoxically-effective amount of an anti-p53 antisense OLIGOTRIP which has a base sequence complementary to that of a p53 target gene present in the cells of the p53-positive cancer.

The time of exposure required to obtain complete elimination of the targeted cells in the bone marrow specimen varies depending on tumor cell target, and must be determined empirically. However, exposure times vary from 1 hour to 4 days or longer. Following exposure to the therapeutic anti-p53 OLIGOTRIP preparation, the autologous bone marrow purged of all p53 positive malignant cells is transplanted back into the donor.

Alternatively, if the opportunity or need to use the OLIGOTRIP-treated marrow sample is not immediate, the purged bone marrow cells can be frozen and stored until needed. Procedures for preparing and storing bone marrow samples frozen in a viable state are discussed in detail in U.S. Pat. Nos. 4,107,937 and 4,117,881.

4. Antisense OLIGOTRIP treatment of peripheral blood-derived stem cells.

The circulating peripheral blood contains a substantial number of mononuclear cells which have the potential to regenerate the complete function of the bone marrow compartment of a host organism, such as a human. These peripheral "stem" cells can be isolated, concentrated, and reintroduced via injection into the peripheral circulation as a "stem cell transplant."

Autologous peripheral blood stem cell transplantation has been found important in facilitating recovery of functional bone marrow after high-dose therapy for a variety of malignant diseases. Autologous peripheral blood stem cell transplantation offers certain advantages to autologous bone marrow transplantation, since the general anesthesia used during bone marrow harvesting can be avoided, the collections of peripheral stem cells can be made in an outpatient setting, and the risk of contamination of the transplanted product with malignant cells appears to be less.

Methods for purging the peripheral stem cell suspension of contaminating tumor cells are very similar, if not identical, to the procedures outlined above for purging bone marrow cells with anti-p53 antisense OLIGOTRIPs.

It is impossible to determine, prior to a patient's receiving the autologous bone marrow or peripheral stem cell transplant, whether a series of radiotherapy or chemotherapy treatments has completely rid that patient of all p53-positive malignant cells. Therefore, another embodiment of the present invention is to provide a course of systemically-administered antisense oligotherapy as an adjunct therapy to the individual who received the transplant of autologous bone marrow cells or peripheral stem cells.

Of course, in order for the tumor cell targets to be effectively inhibited by the selected antisense OLIGOTRIPs, the cells must be exposed to the OLIGOTRIPs under conditions that facilitate their uptake by the malignant cells. This may be accomplished by a number of procedures, including, for example, simple incubation of the cells with the OLIGOTRIPS in a suitable nutrient medium for a period of time suitable to achieve selective inhibition of the malignant cells. According to the present invention, incubation of bone marrow cells with selected OLIGOTRIPs (anti-p53 OLIGOTRIP, for example) inhibits proliferation of cells after about 8 hours exposure (and possibly sooner). Incubation for at least about 7–10 days kills fresh malignant cells (leukemic blasts, for example) but has no significant effect on fresh cells from normal bone marrow. Accordingly, a preferred procedure for practice of the invention involves placing bone marrow cells into culture, for example, as described by Meagher et al. (Blood 72: 273, 1988) or U.S. Pat. No. 4,721,096, and then incubating with an optimal concentration of the selected antisense OLIGOTRIP.

The concentration of OLIGOTRIP to be used may vary, depending upon a number of factors, including the type of cancerous cells present in the marrow, the type, and specificity of the particular antisense OLIGOTRIP(s) selected, and the relative toxicity of the OLIGOTRIP for malignant and normal bone marrow cells. Although it is expected that, according to the present invention, there is significant inhibition of tumor cell DNA synthesis at OLIGOTRIP concentrations as low as 30 micromolar, optimal inhibition is expected to be observed at concentrations of at least 60 micromolar. With the aid of the techniques set forth in the present disclosure, those of skill in the art should be able to determine the optimal concentration to be used in a given case.

After the marrow cells have been exposed to the OLIGOTRIP and, in some cases, cultured as described above, they are then infused into the transplant recipient to restore hemopoiesis.

EXAMPLES

The following examples further demonstrate the various embodiments of this invention.

EXAMPLE 1

Synthesis of TRIP Bases

The interstrand nucleotide base pair structures to which the TRIPs specifically associate by hydrogen bonding are shown in FIGS. 4 and 5; the routes for synthesis of the novel TRIP base moieties are shown in FIGS. 10–13 and 15 (FIG. 18 grant proposal). All synthetic intermediates are characterized and confirmed by nuclear magnetic resonance, ultraviolet light absorption, infrared light absorption, and mass spectroscopy.

The chromatographic properties of the TRIPSIDEs and the corresponding TRIPTIDEs (5'- and 3'-monophosphates) are determined using reverse phase and ion exchange high-pressure liquid chromatography (HPLC) and capillary electrophoresis. These analytical methods are important in confirming the stability and composition of OLIGOTRIPs (see below).

Set forth below is a detailed description of the synthesis of four TRIP bases of the present invention: 1) 4-chloro-anti-GC; 2) 5-chloro-anti-CG; 3) 4-chloro-anti-AT; and 4) 5-chloro-anti-TA. The individual steps in the synthetic process are lettered alphabetically, and refer to the letters in the pathway of FIG. 10, FIG. 11, FIG. 12, and FIG. 13.

Figure 10:
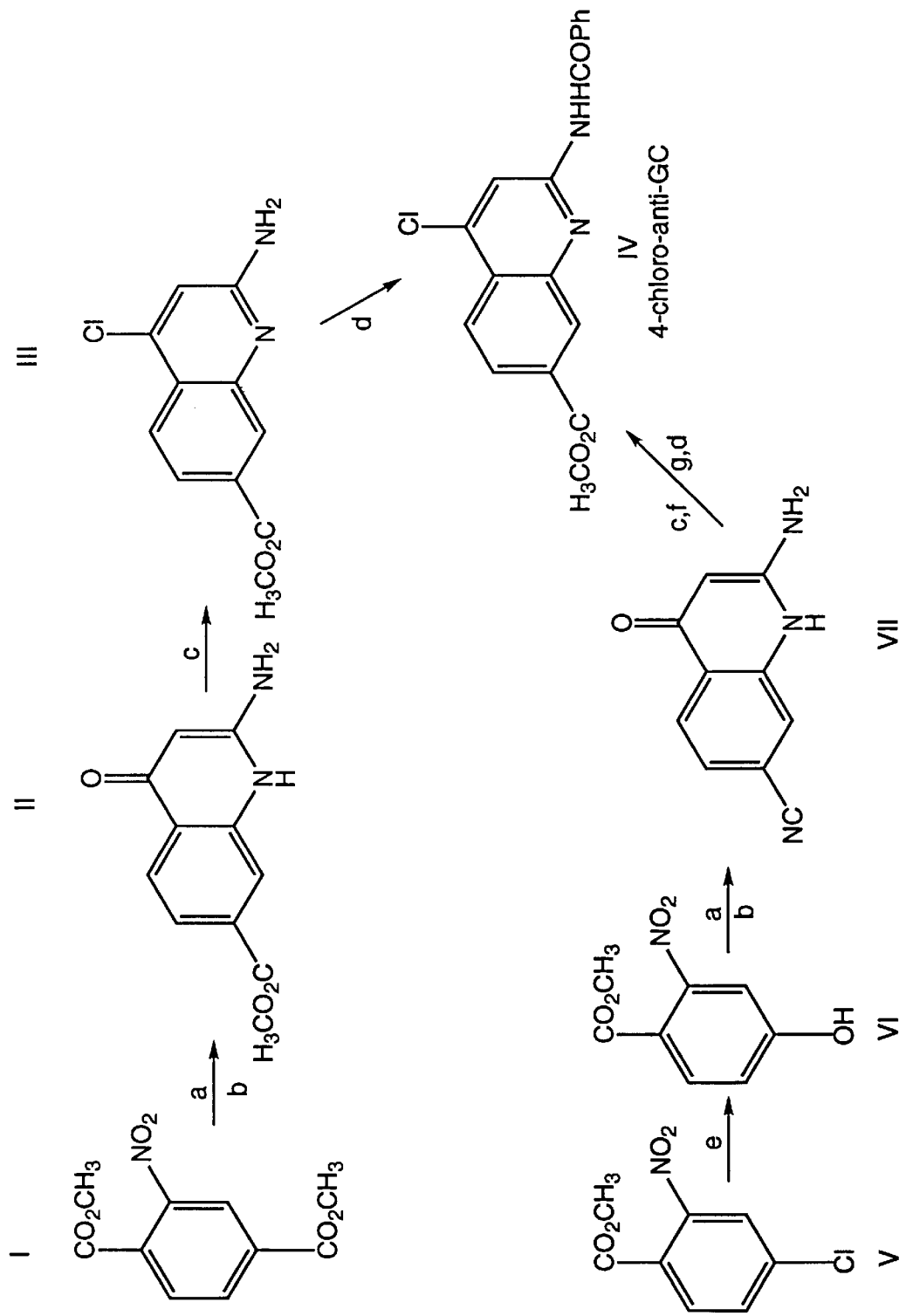
FIG. 10 demonstrates the pathway for synthesizing the novel TRIP of the present invention, 4-chloro-anti-GC.

1. Synthesis of the "4-chloro-anti-GC" TRIP base (FIG. 10)

Step a. Dimethyl nitroterephthalate (COMPOUND I) (1 equivalent) and cyanoacetic (1.1 equivalent) are reacted at room temperature (heating as necessary) with sodium methoxide (1.1 equivalent) in methanol. The product is purified by column chromatography and/or crystallization.

Step b. The resulting nitro intermediate is reduced by stirring with Rainey nickel catalyst under a hydrogen atmosphere (40 p.s.i.) in acetic acid or ethanol solvent to produce the bicyclic quinoloid compound (COMPOUND II). This product (which is 2-amino-7-carbomethoxy-4(1H)- quinoline) is purified by column chromatography and/or crystallization. It should be noted that COMPOUND II contains a methyl protecting group on the substituent at position 7. Other protecting groups can be employed. Such protecting (blocking) groups are well known in the art, and need not be detailed here.

Step c. The vinylogous amide (1 equivalent) is dehydrated to the chloro quinoline (COMPOUND III) by reaction with phosphoryl chloride (0.7 equivalent) in pyridine with heating as required. Purification is enhanced by column chromatography and/or crystallization.

Step d. The amine (1 equivalent) dissolved in pyridine is slowly treated with benzoyl chloride (1.1 equivalent) at room temperature and then with heating to yield the desired amide derivative (COMPOUND IV), which is 2-benzamido-4-chloro-7-carbomethoxyquinoline. This product is purified by column chromatography and/or crystallization.

Step e. Another route to 4-chloro-anti-GC is from the methyl 3-nitro-4-chlorobenzoate (COMPOUND V) (1 equivalent) treated with cuprous cyanide (1.1 equivalent in dimethyl sulfoxide (or pyridine) solvent). Heat as necessary. The product (COMPOUND VI) is purified by column chromatography and/or crystallization.

Step f. The synthesis then follows essentially the same pathway as detailed above, except the nitrile functionality is hydrolyzed by heating in concentrated sulfuric acid to yield the acid (COMPOUND VII) which is purified by column chromatography and/or crystallization.

Step g. The acid is then converted into the methyl ester by refluxing in anhydrous methanol in the presence of anhydrous hydrogen chloride. This product (COMPOUND IV) is purified by column chromatography and/or crystallization.

Figure 11:
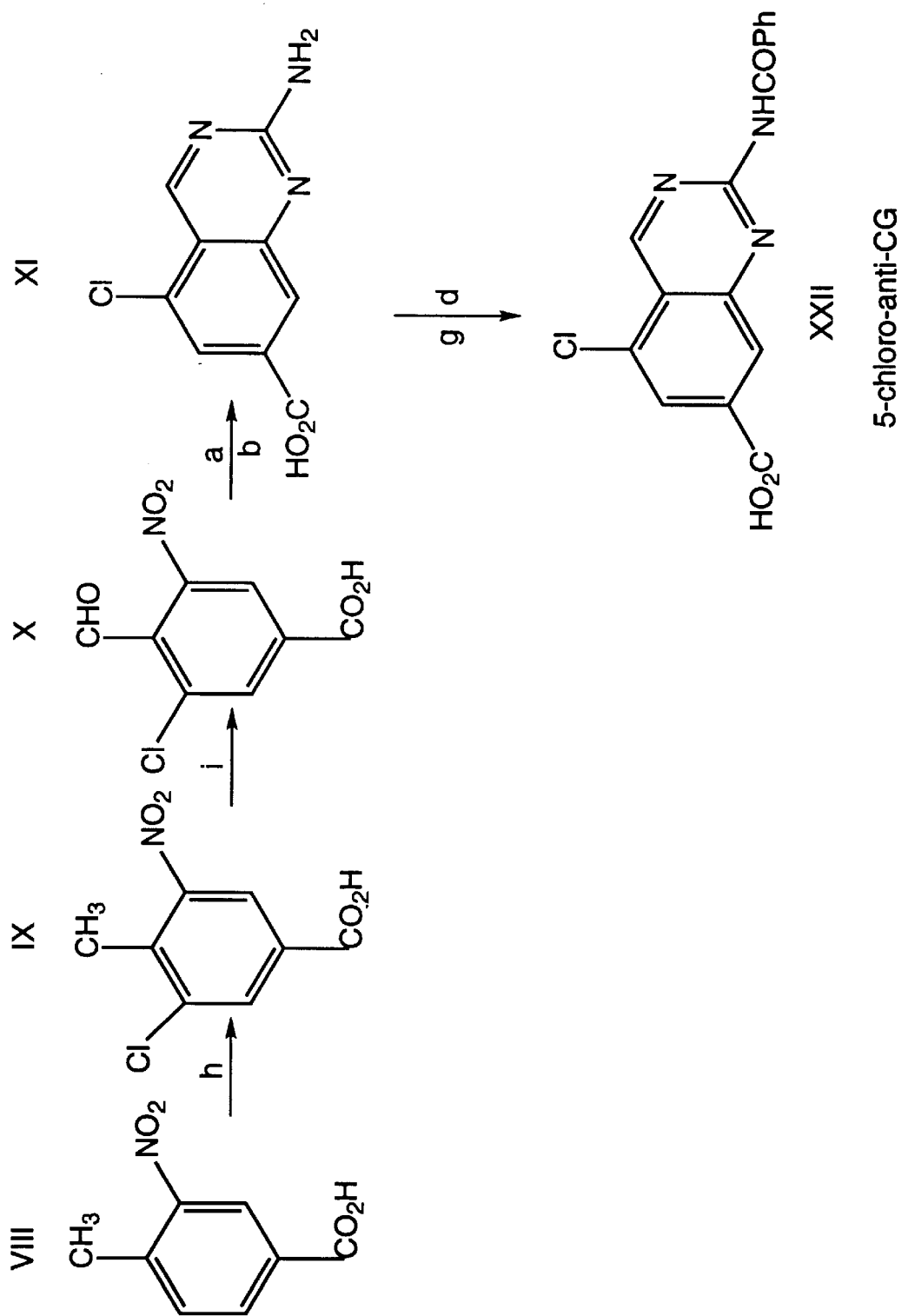
FIG. 11 demonstrates the pathway for synthesizing the novel TRIP of the present invention, 5-chloro-anti-CG.

2. Synthesis of the "5-chloro-anti-CG" TRIP base (FIG. 11).

Step h. 3-Nitro-4-methylbenzoic acid (COMPOUND VIII) (1 equivalent) is chlorinated by treatment with cupric chloride in carbon tetrachloride (or by chlorine in the presence of ferric chloride catalyst). This product (COMPOUND IX) is purified by column chromatography and/or crystallization.

Step i The aromatic methyl group of the resulting 3-nitro-4-methyl-5-chlorobenzoic acid (COMPOUND IX) (1 equivalent) is then oxidized by slow addition of chromyl chloride (1.1 equivalent) in carbon tetrachloride at room temperature. The reaction is then refluxed for several hours and then worked up by quenching in water and washing with dilute acid. This product (COMPOUND X) is purified by column chromatography and/or crystallization.

Steps a, b, g and d are then repeated as described above to yield first (COMPOUND XI), and then the desired 5-chloro-anti-CG quinoline derivative (COMPOUND XIII) (wherein R' is methyl that is ready for conversion into the TRIPSIDE. These intermediate products are purified by column chromatography and/or crystallization.

Figure 12:
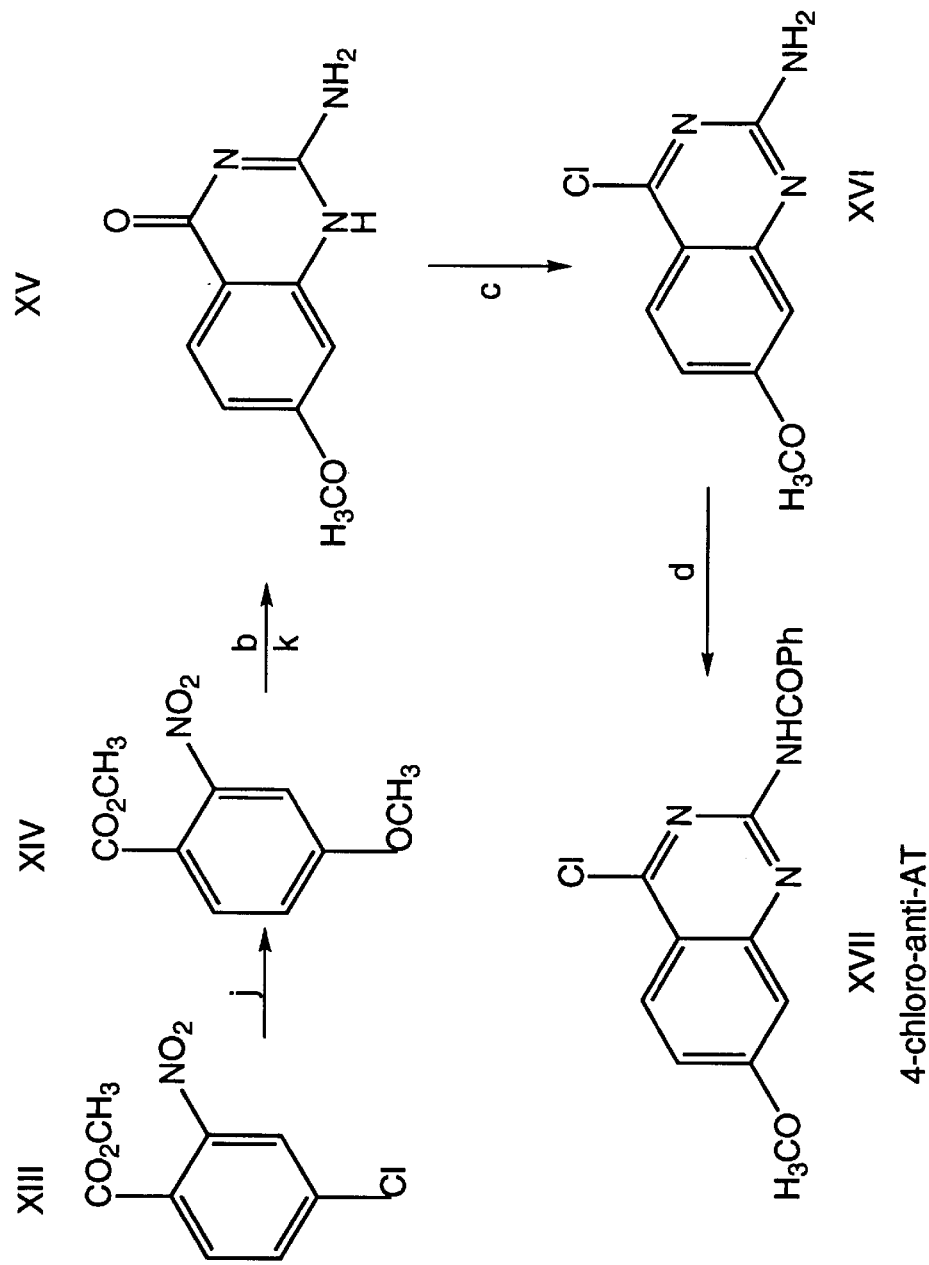

3. Synthesis of the "4-chloro-anti-AT" TRIP base (FIG. 12).

Step j. Methyl 3-nitro-4-chlorobenzoate (COMPOUND XIII) (see above for synthesis of 4-chloro-anti-CG) (1 equivalent) is treated with sodium methoxide (1.1 equivalent) in methanol with heating to produce the methyl 3-nitro-4-methoxybenzoate (COMPOUND XIV) which is purified by column chromatography and/or crystallization.

Step k. The nitro group is then reduced with Rainey nickel (step b) and the resulting amine (1 equivalent) condensed with guanidine hydrochloride (1.1 equivalent) with $NH_2C(=NH)NH_2$ in methanol containing sodium methoxide 1.5 equivalent). The product (COMPOUND XV) is purified by column chromatography and/or crystallization.

The vinylogous amide is dehydrated as described above (step c) and the product (COMPOUND XVI) is purified by column chromatography and/or crystallization.

The resulting quinazoline is benzoylated with benzoyl chloride as described above (step d). The final product (COMPOUND XVI) is 2-benzamido-4-chloro-7-methoxyquinazoline, and it is purified by column chromatography and/or crystallization.

Figure 13:
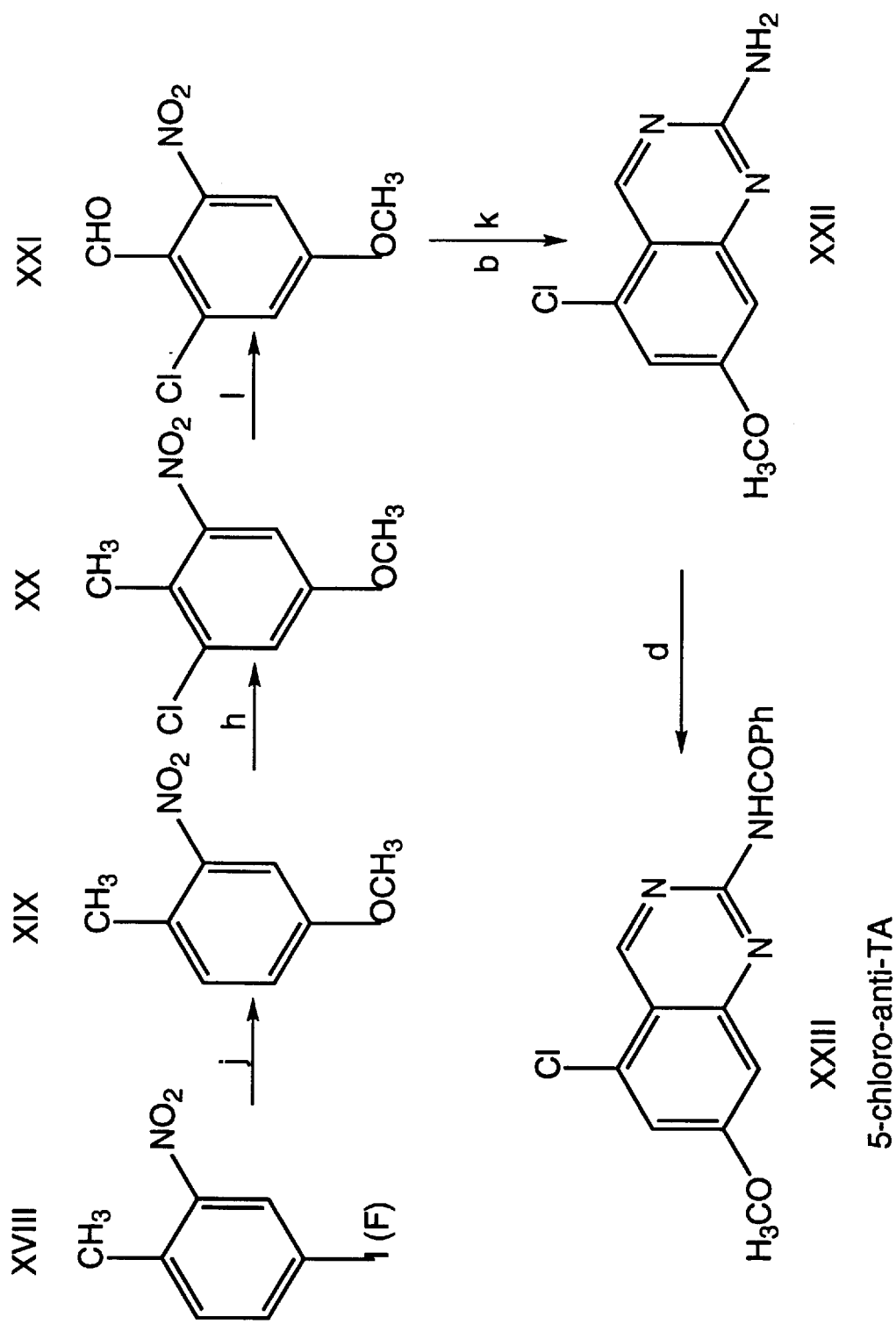
FIG. 13 demonstrates the pathway for synthesizing the novel TRIP of the present invention, 5-chloro-anti-TA.

4. Synthesis of the "5-chloro-anti-TA" TRIP base (FIG. 13).

2-Methyl-5-iodonitrobenzene (COMPOUND XVIII) (1 equivalent) is converted to the methoxy compound as described above (step j) and the product (COMPOUND XIX) is purified by column chromatography and/or crystallization.

Chlorination is carried as described above (step h) and the product (COMPOUND XX) is purified by column chromatography and/or crystallization.

The 2-methyl-3-chloro-5-methoxynitrobenzene is oxidized to the aldehyde as described above (step i) and the product (COMPOUND XXI) is purified by column chromatography and/or crystallization.

Step 1. The nitro group of 2-nitro-4-methoxy-6-chlorobenzaldehyde (1 equivalent) is reduced to the amine by refluxing in benzene or ethanol with iron powder (the powder having been pretreated with concentrated hydrochloric acid). This amine is then treated with guanidine hydrochloride as described above (step k) to yield the quinazoline (COMPOUND XXIII) which is purified by column chromatography and/or crystallization. Benzoylation of this product is performed as described above (step d), to yield COMPOUND XXII.

Figure 15:
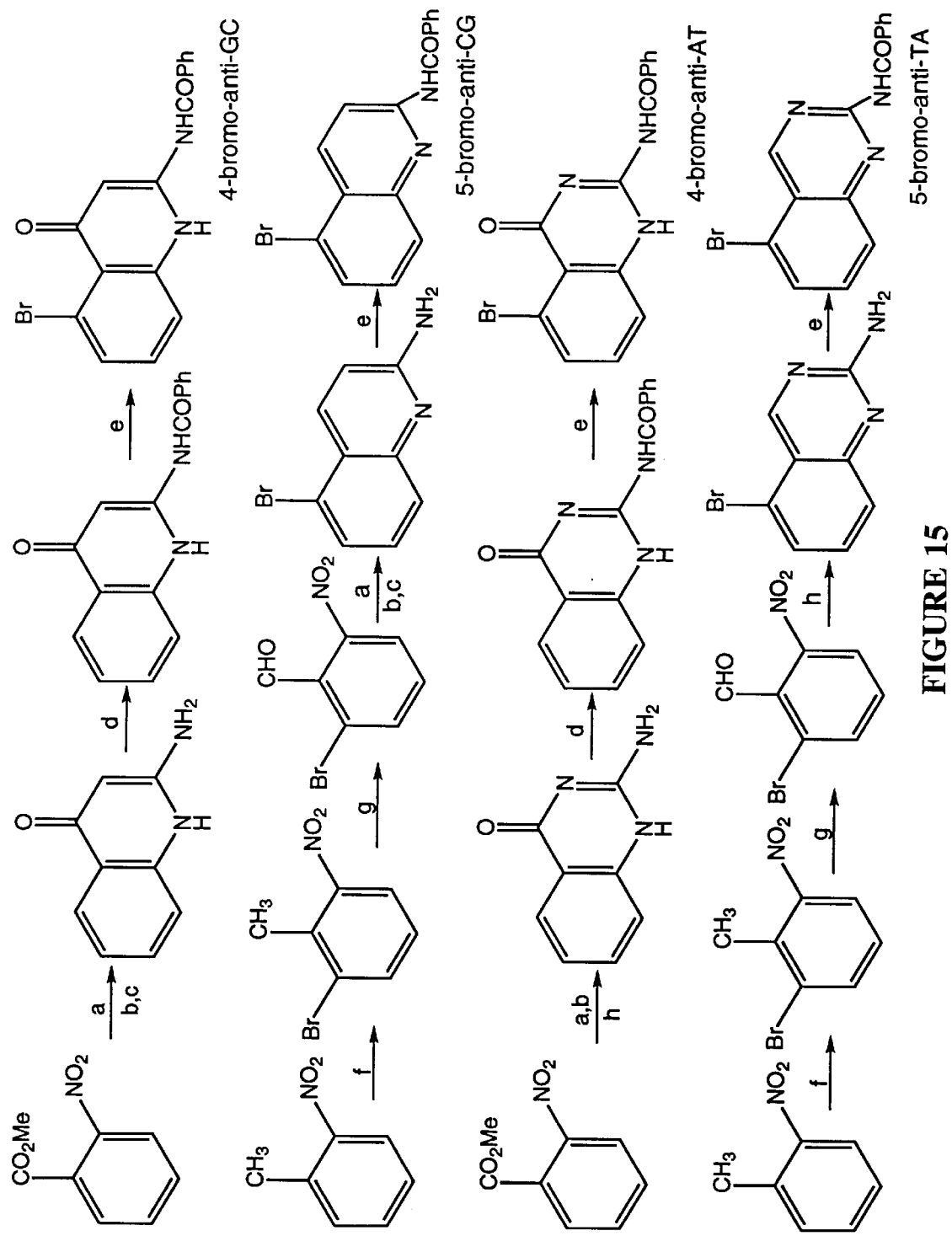
FIG. 15 diagramatically illustrates alternative pathways for synthesizing novel TRIPs of the present invention, which are 4-bromo-anti-GC; 5-bromo-anti-CG; 4-bromo-anti-AT; 5-bromo-anti-TA. Lower-case letters accompanying arrows in the figure refer to steps in the respective syntheses as listed in the lower portion of the figure.

In a specific embodiment, brominated TRIPs are prepared according to the synthetic methods summarized in FIG. 15. The synthetic steps are indicated by letters, as summarized below:

a. Fe/HCl
b. $HO_2CCH_2CN/CH_3ONa$/heat
c. $H_2SO_4/H_2O$
d. PhCOCl
e. $POBr_3$
f. $FeBr/Br_2$
g. $CrO_2Cl_2$
h. $NH_2C(=NH)NH_2$ Using the synthetic schemes summarized in FIG. 15, the following TRIPs are produced: 4-bromo-anti-GC, 5-bromo-anti-CG, 4-bromo-anti-AT, 5-bromo-anti-TA.

EXAMPLE 2

Synthesis of the Novel TRIPSIDEs of the Present Invention

Figure 14:
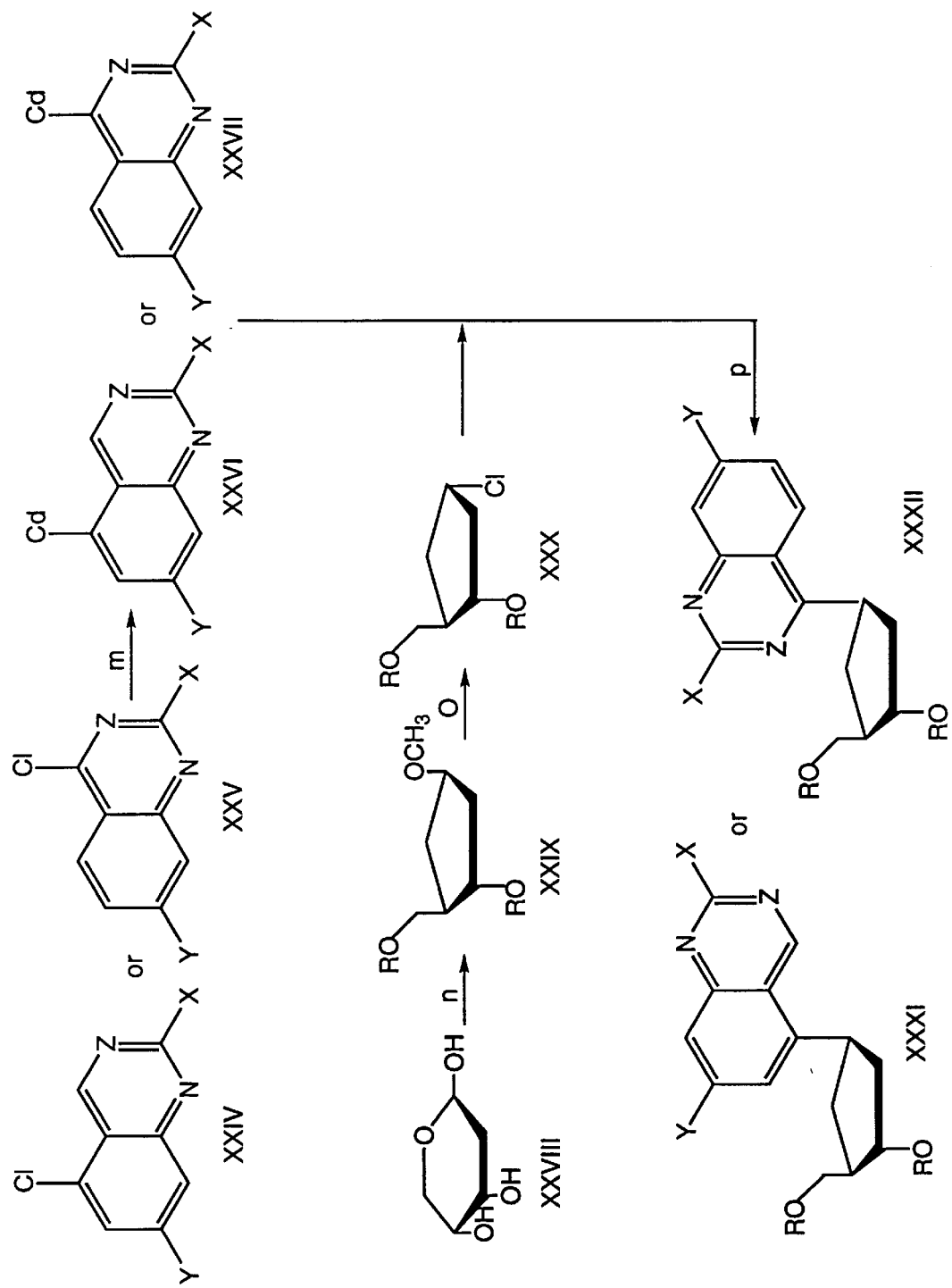
FIG. 14 shows the synthesis of the deoxyribose sugar-containing TRIPSIDEs from the TRIP bases.

Step m. The four chloro compounds (4-chloro-anti-GC (COMPOUND IV), 5-chloro-anti-CG (COMPOUND XII), 4-chloro-anti-AT (COMPOUND XVII) and 5-chloro-anti-TA (COMPOUND XXIII)) (1 equivalent) are converted into their corresponding 2'-deoxy-nucleoside derivatives in diethyl ether by treatment with n-butyllithium (1.2 equivalent) in hexane at room temperature followed by heating at reflux temperature. After about 1 hour, cadmium chloride (0.7 equivalent) is added and the resulting suspension refluxed for several hours and the ether solvent removed in vacuo. In FIG. 14, COMPOUNDS XXIV and XXVI represent the quinazoline compounds when Z is a nitrogen, and represent the quinoline compounds when Z is a carbon. Similarly, COMPOUND XXV and XXVII represent the quinazoline compounds when Z is a nitrogen, and represent the quinoline compounds when Z is a carbon.

Steps n, o, and P. The resulting residue is then treated with 2-deoxy-3,5-di-O-acetyl-D-ribosyl chloride (COMPOUND XXX) (0.6 equivalent) (prepared by the method of Ness et al., J. Org. Chem. 26: 2895, 1961) dissolved in dry toluene and the suspension refluxed for several hours. The products are purified by column chromatography and/or crystallization. In FIG. 14, COMPOUNDS XXXI and XXXII represent the quinazoline compounds when Z is a nitrogen, and represent the quinoline compounds when Z is a carbon.

In especially preferred embodiments of the present invention, the resulting 2'-deoxynucleoside derivatives are: 2-amino-4-(2'-deoxy-beta-D-ribofuranos-1-yl)-7-hydroxyquinazoline (which is "anti-AT"); 2-amino-5-(2'-deoxy-beta-D-ribofuranos-1-yl)-7-hydroxyquinazoline (which is "anti-TA"); 2-amino-4-(2'-deoxy-beta-D-ribofuranos-1-yl)-7-carboxyquinoline (which is "anti-GC"); and 2-amino-5-(2'-deoxy-beta-D-ribofuranos-1-yl)-7-carboxyquinoline (which is "anti-CG"). The "-yl" term in these chemical descriptions refers to the position of sugar attachment to the TRIP moiety.

Figure 16:
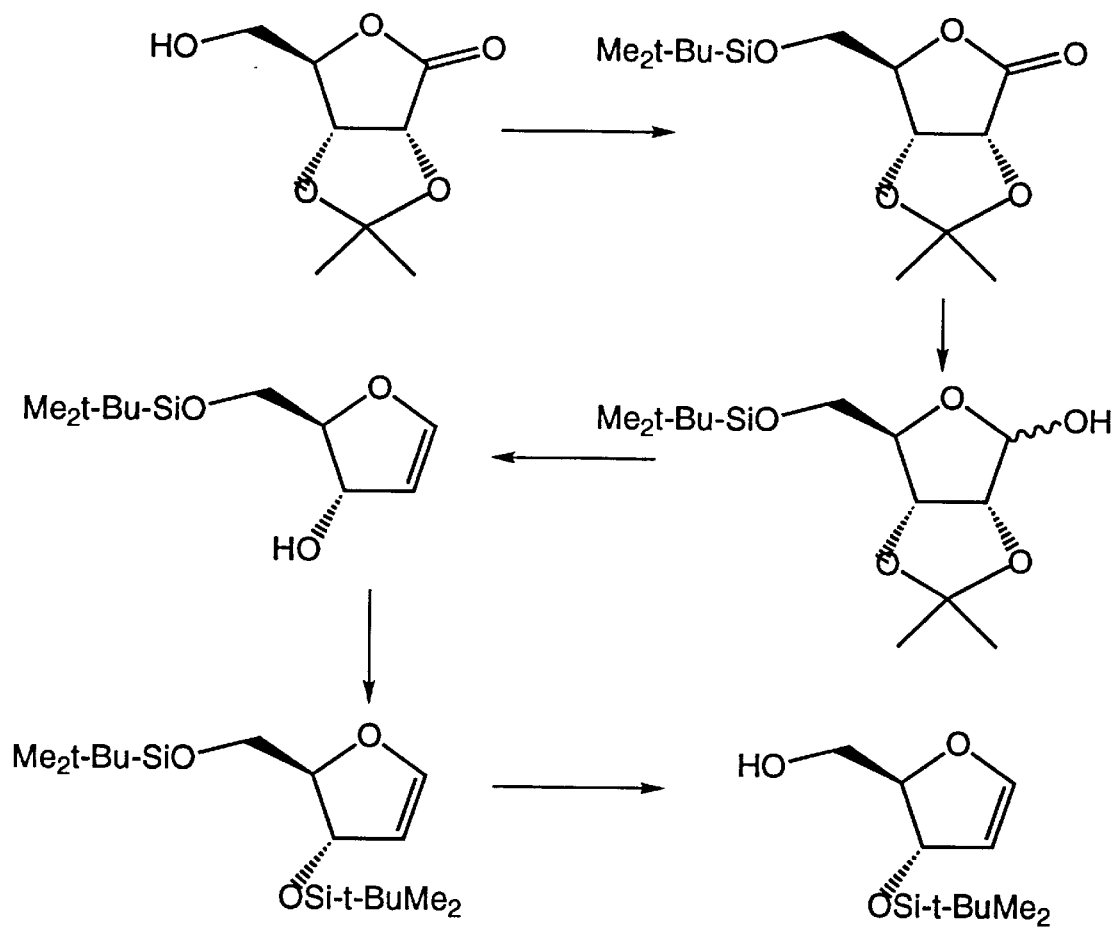
FIG. 16 shows the synthesis of a deoxyribose synthon, which is coupled with TRIP bases to form TRIPSIDEs of the invention.
Figure 17:
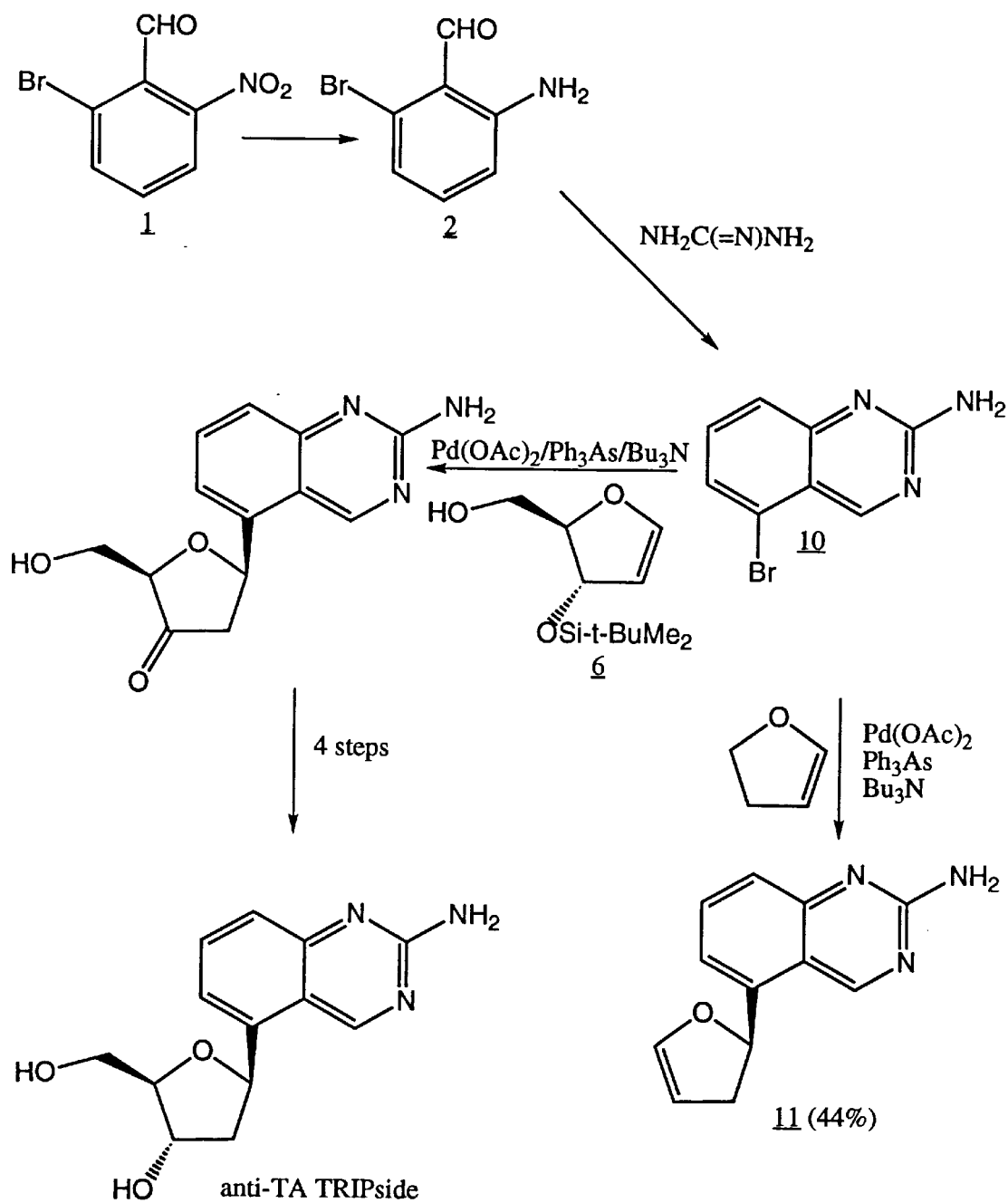
FIG. 17 shows an alternative synthesis of an anti-TA TRIPSIDE of the invention.

Alternative methods for synthesizing TRIP deoxyribose synthons and TRIPSIDEs of the present invention are set forth schematically in FIGS. 16 and 17, wherein syntheses of anti-AT TRIPSIDE is exemplified. These syntheses were performed according to the methods of Cheng et al. J. Org. Chem. 50: 2778–2780, 1985; Farr et al., Carbohydrate Chemistry 9: 653–660, 1990; Zhang & Davies, J. Org. Chem. 57: 4690-4696, 1992; and Farr et al., J. Org. Chem. 57: 2093–2100, 1992. In these procedures, it should be noted that the key step is the coupling of the TRIP with the deoxyribose synthon. The procedure is based on the preparation of protected ribofuranoid glycals as described by Cheng et al., 1985, supra, and employs a selective Ireland reductive fragmentation ($Li/NH_3$) of the 2'-3'-isopropylidine group in compound 3 of FIG. 16 (Ireland et al., J. Org. Chem. 43: 786–787, 1978). In turn, the ultimate reagent for the coupling steps (compound 6 of FIG. 17) is regio- and sterio-specifically attached to the heterocycle using $Pd(OAc)_2$ catalyst in the presence of $Ph_3P$ or $Ph_3As$ ligands. These methods have been used to prepare a variety of C-glycosides in multi-gram amounts with yields in the range of 40–80%.

Using the above-described procedures, a coupling reaction was performed with anti-TA TRIP and 2, 3-dihydrofuran, the latter being a model for the complex deoxyribose synthon shown in FIG. 16 (see FIG. 17 for the synthetic scheme). In this procedure, the $N^2$-amino group of anti-TA was protected as the dibenzyl derivative. Yields of greater than 40% were obtained with no adjustments to the procedure, and the same procedure was used to prepare anti-TA TRIPSIDE in greater than 50% yield. These structures were confirmed by UV, $^1H$ and $^{13}C$-NMR and FAB/MS. As expected, the procedure afforded only the desired β-anomer. Removal of the benzyl protecting group was accomplished by $RuO_4$ oxidation (Gao & Jones, J. Am. Chem. Soc. 109: 1275–1278, 1987).

In addition to the above-described procedures, the coupling of unprotected anti-TA TRIP with 2, 3-dihydrofuran has been achieved, with good yield. A key factor in the yield of the coupling reaction has been found to be the use of little, if any, DMF solvent. Elimination of the need for protection and deprotection is of great advantage, as it removes two difficult steps in the synthesis. Thus, the $N^2$-amino group of the phosphoramidite may be protected as the benzoyl amide during OLIGOTRIP synthesis. However, it may not be necessary to protect the unreactive amino groups of anti-TA and anti-AT TRIPs using H-phosphonate-based oligomer synthesis.

EXAMPLE 3

Conversion of 2'deoxy-TRIPSIDEs into Phosphoramidite Intermediates

The 2'-deoxy-TRIPSIDEs of this invention are converted into the phosphoramidites required for OLIGOTRIP oligomer synthesis as follows:

1. The 3',5'-O-acetyl protecting groups of the 2'-deoxy-TRIPSIDEs are removed by gentle treatment with ammonia in methanol so that the quinoline and quinazoline benzoyl protecting groups are left intact. The unprotected 2'-deoxy-TRIPSIDE in pyridine, containing 0.05 equivalents of dimethylaminopyridine and 1.4 equivalents of triethylamine, is then treated with 1.2 equivalent of 4,4'-dimethoxytrityl chloride (DMTrCL). More DMTrCL is added until thin layer chromatography shows the reaction to be complete. The 5'-DMTr-2'deoxy-TRIPSIDE product is purified by column chromatography and/or crystallization.

The structures of the protected TRIPSIDEs anti-TA (COMPOUND XXIII) and anti-AT (COMPOUND XVII) contain aromatic methyl ethers which must be removed and replaced by a more labile protecting group. The methyl group is removed by treatment of the compound with $Me_3SiI$ in $CHCL_3$ (Jung & Lyster, J. Org. Chem. 42: 3761, 1977; Minamikawa & Brossi, Tetrahedron Lett., p. 3085, 1978) and esterification of the resulting phenol with PhCOCl. This protecting group is stable to conditions used to hydrolyze the aliphatic sugar acetate groups that are required to functionalize 5'-O and 3'(or 2')-O with the 5'-O-dimethoxy-trityl (DMTr) derivative and phosphoramidite reagent, respectively. Removal of the O-benzoyl group (or any other suitable protecting group which may have been used) is performed during the $NH_4OH$ cleavage and deprotection of oligomer.

2. Conversion to TRIP-phosphoramidites. The protected 5'-DMTr-2'-deoxyTRIPSIDEs are converted into the phosphoramidite form by reaction in pyridine, containing diisopropylethylamine (4 equivalents) and methylene chloride, with commercially available 2-cyanoethyl N,N-diisopropylchlorophosphoramidite or methyl N,N-diisopropylchlorophosphoramidite (1 equivalent) dissolved in methylene chloride containing diisopropylethylamine. This is stirred at room temperature and the reaction monitored by thin-layer chromatography. The product is purified by column chromatography. Preparation of 5'-O-trityl-2'-O-phosphoramidite derivatized 3'-deoxyTRIPSIDEs follows the same synthetic route. These compounds are then used in a commercial DNA synthesizer using standard operating procedures, for the synthesis of OLIGOTRIPs.

EXAMPLE 4

Preparation of TRIP-Phosphorothioate Compounds

The phosphorothioate OLIGOTRIPs of the present invention are prepared by reacting the phosphite intermediate with tetraethylthiuram disulfide in lutidine rather than with $I_2$. It is also possible to specifically cleave the backbone at a phosphorothioate linkage with iodoethanol (Gish & Eckstein, Science 240: 1520, 1988) via a triester intermediate. The normal phophodiester backbone is relatively stable to this reagent.

The OLIGOTRIP with hydrogen phosphate backbone is made using machine compatible H-phosphorate chemistry. It is then converted into the thioate by treatment with $S_8$ (Stein et al., Anal. Biochem. 188: 11, 1990). This method is used to prepare the $^{35}$S-labeled thioate OLIGOTRIP and the normal phosphodiester OLIGOTRIP with a 5'-$^{35}$S-labeled thiophosphate terminus.

EXAMPLE 5

Preparation of Oligomeric OLIGOTRIPs

The solid support derivatized with the desired 3'-end TRIP is prepared by coupling the 3'-O-succinate derivative of the TRIPSIDE to the primary amino groups of commercially available aminomethyl polystyrene resin. This allows for 100–200 μmol of TRIPSIDE per gram of resin. The actual machine synthesis on an Applied Biosystems, Inc. instrument follows the normal DNA protocols, although coupling conditions and yields are confirmed. The electrophoretic mobility of these oligomers is determined by polyacrylamide gel and capillary electrophoresis. The protecting groups are all labile to the type of $NH_4OH$ treatment normally used to remove the oligomer from the solid support and to remove protecting groups. Because the TRIPs are C-glycosides, their lability to acid treatment during removal of DMTr protecting groups is low.

Even though the TRIPSIDEs are relatively stable to acidic conditions, it is critical to determine if isomerization at the anomeric carbon occurs during any of the deprotection steps. To accomplish this, the TRIPSIDEs are treated at pH 2.0 to 12.0 (increments of 1.0 pH unit) and at 20° to 60° C. (increments of 5° C.) for varying periods of time (up to 48 h), and then analyzed by HPLC and spectroscopic methods (UV, NMR) to determine their stability to the different conditions.

The stability of OLIGOTRIPs toward Serratia marcescens endonuclease, exonuclease III, mung bean nuclease, nuclease $P_1$ and nuclease $S_1$ may also be determined by analysis of the OLIGOTRIPs by HPLC, laser desorption/mass spectrometry and polyacrylamide gel electrophoresis. It is believed that the OLIGOTRIPs with the quinoline or quinazoline bases will be generally resistant to enzyme digestion. This is an important issue if the compounds are to be used in biological systems.

Since traditional sequencing is not possible on the synthetic compounds of the invention, the composition and sequence of small OLIGOTRIPs ($\leq$6 TRIPS) will be determined by FAB tandem- and laser desorption time-of-flight mass spectroscopy. OLIGOTRIPs greater than 6-mers may be analyzed by the time-of-flight instrument, which can provide molecular weight determinations of $\geq$330,000 Daltons on pmol levels of material.

EXAMPLE 6

Preparation of End-Labeled OLIGOTRIPs

It is convenient to be able to enzymatically end-label the OLIGOTRIPs using polynucleotide kinase and alkaline phosphatase in the process. Many chemically-modified 5'-hydroxy-3'-monophosphate nucleotides, including those containing large bulky adducts, are substrates for T4 kinase, although phosphorylation conditions may need to be adapted. When they are not substrates, it is necessary to chemically radiolabel the backbone with $^{35}$S. this is accomplished by treating hydrogen phosphonate backbone OLIGOTRIPs with $^{35}$S (Stein et al., Anal. Biochem. 188: 11, 1990).

Synthesis of 5'-$^{35}$S-end-labeled OLIGOTRIP.

Specific 5'-end-labeling with $^{35}$s is done using hydrogen phosphonate chemistry, with adamantine carbonyl chloride activation (Schreiber et al., Nuc. Acids Res. 13: 7663, 1985), and 2-$ClCH_2CH_2OPHO_2^-$at the last step in the machine synthesis. The DNA synthesizer is re-programmed to do this. The resulting H-phosphonate is then treated with $^{35}S_8$ as previously described to afford the $5'^{35}S$-phosphorothioate-OLIGOTRIP. Thus, when enzymatic labeling is not effective, this method is used to chemically prepare 5'-labeled OLIGOTRIPs.

EXAMPLE 7

Preparation of OLIGOTRIPs Linked to an Intercalator

Acridine is coupled to the primary amino group of a hexamethyleneamino linking arm connected to the 5'-end of an OLIGOTRIP via a $(CH_2)_5$ tether using phosphoramidite chemistry previously described (Thuong & Chassignol, Tetrahedron Lett. 29: 5905, 1988). This intercalator is used because: 1) its attachment to the OLIGOTRIP is straightforward; 2) it shows little preference for A—T or G—C sites; and 3) it has excellent absorption and fluorescence properties that allow it to be used as a marker for intercalation. Intercalation of the acridine nucleus into a DNA base pair stack causes a hypochromic shift. The final product is purified by HPLC. The addition of the intercalator further stabilizes any triple helix interaction and increases the lipophilicity of the OLIGOTRIPs.

EXAMPLE 8

Preparation of OLIGOTRIPs Connected to a DNA Cleaving Agent

The attachment of a DNA cleaving agent that can be activated in a controlled fashion has been very useful in examining the binding specificities of traditional DNA triple helix molecules. A modified TRIP is prepared that is appended with a phenanthroline that can chelate copper and generate poorly diffusible reactive oxygen species cable of cleaving DNA (Chen & Sigman, Proc. Natl. Acad. Sci. USA 83: 7147, 1986; Chen & Sigman, J. Amer. Chem. Soc. 110: 6570, 1988). Using previously detailed synthetic procedures, a 5-(6'-bromohexanoamido)-1,10-phenanthroline (Thuong & Chassignol, Tetrahedron Lett. 28: 4157, 1987) is attached to the 5'-end of an OLIGOTRIP modified with a phosporothioate terminus (Francois et al., Proc. Natl. Acad. Sci. USA 86: 9702, 1989). The terminal functionality, $HSP(O_2)O$—, is prepared by using bis(2-cyanoethyl)-N,N-diisopropylphosphoramidite at the last step in the machine synthesis and oxidizing the intermediate phosphite with tetraethylthiuram disulfide. This approach can be used to functionalize any OLIGOTRIP and is used to determine the sequence-specific interaction of the OLIGOTRIP with different duplex DNA's (see below).

EXAMPLE 9

Preparation of OLIGOTRIPs Connected to a DNA Alkylating Agent

The attachment of a DNA alkylating functionality, N-methylnitrosourea (MNU), onto the 5'-terminus of an OLIGOTRIP may be done in two steps. The first step is to incorporate an Fmoc-protected amine (FIG. 19 Grant Application) onto the 5'-terminus of an OLIGOTRIP. The oligomer is then removed from the solid support and fully deprotected with base, and the OLIGOTRIP with the 1° amino terminus purified by HPLC. The amino group of the OLIGOTRIP is then condensed with N-hydroxysuccinimidyl N-methyl-N-nitrosocarbamate (Martinez et al., J. Med. Chem. 25: 178–182, 1982) in DMF/$H_2O$ to afford the desired N-methyl-N-nitrosourea terminus. The DNA is purified by HPLC using water (or an aqueous volatile buffer, pH 5.0) with the appropriate organic phase on a C18 column. The quantitative determination of the nitrosourea functionality is achieved by a modification of the Griess calorimetric assay that involves acid-catalyzed denitrosation of a known amount of MNU-OLIGOTRIP and quantitation of the $NO_2$ (Preussmann et al., In *N-Nitrioso Compounds: Analysis and Formation*; P. Bogorski, Ed.; LARC, Lyon; p. 81; 1972). Using the same amino terminus, other alkylating moieties may be attached to OLIGOTRIPs. An OLIGOTRIP with a MNU appendage may be used to determine the sequence specific interaction of an OLIGOTRIP with different duplex DNA's (see below).

EXAMPLE 10

DNA Binding and Sequence Specificity of OLIGOTRIPs

A. Characterization of binding of OLIGOTRIPS.

The characterization of poly(anti-TA)$_n$ is described in detail below. Analogous procedures may be performed with the other homo- and hetero-OLIGOTRIPs using the appropriate duplex DNA (complementary and non-complementary) targets.

The evaluation of the equilibrium binding of OLIGOTRIPs is accomplished by determining the $K_D$ for binding of a homo-OLIGOTRIP (e.g. all anti-TA) to selected synthetic DNA duplexes using a gel shift assay. The goal of these relatively straightforward experiments is to determine if oligomers of different lengths bind with $K_D$'s of $\geq 10_{-8}$M. This is a reasonable benchmark for sequence specific binding. $K_D$'S $\leq 10^{-6}$ are considered to reflect non-specific binding. The binding of the poly(anti-TA)$_n$ OLIGOTRIPs may also be monitored by UV-determined $T_m$ denaturation experiments. Traditional triplex structures show increased melting temperatures due to stabilization of the duplex DNA by the third strand (Manzini et al., J. Mol. Biol. 213: 833–843, 1990. Cooney et al., Science 241: 456–459, 1988).

These binding analyses with poly(anti-TA)$_n$ OLIGOTRIPs are designed to demonstrate that the oligotrip is functioning as intended, i.e. poly(anti-TA)$_n$ only binds tightly to a target with an embedded poly(dA):poly(dT) stretch; weak interactions are observed with hetero A—T targets and with G—C targets. The binding of the OLIGOTRIP anti-TA (of various lengths) via a triple-helix motif can be compare with that of the natural pyrimidine triple helix of the same length. Accordingly, poly(anti-TA)$_n$ may be compared with poly d(T)$_n$. The binding to duplex target is done in the absence and presence of NaCl(50–200 mM) or $MgCl_2$ (10–50 mM).

Binding of OLIGOTRIPs to target duplex DNA sequences may also be assessed by the electrophoretic mobility shift assays decribed below. Binding reactions are performed using end-labeled duplex DNA (50,000 cpm, ca. 1 pmol) in 50 mM Tris-HCl (pH 7.4) containing 5mM NaCl and 10 mM $MgCl_2$, tRNA (1 μL of 1 mg/mL) in a total volume of 10 μL. Reactions are then supplemented with 1 μL of an 80% glycerol solution containing bromophenol blue and are loaded on a 20% native polyacrylamide gel prepared in TBE buffer supplemented with 2–4 mM $MgCl_2$. Electrophoresis is done in this buffer (with recirculation) at 4° C. overnight. The resulting gels are imaged and quantitated on a PhosphoImager or similar device.

The apparent fraction of duplex target bound by probe oligonucleotide (Q) is calculated for each concentration of OLIGOTRIP using the definition:

$$Q = S_{triplex}/(S_{triplex} + S_{duplex}) \quad (1)$$

where $S_{triplex}$ and $S_{duplex}$ represent the signal for triple helical and duplex complexes, respectively. To correct for background effects, the fraction of duplex in triple-helical form is then converted into a scaled score (F):

$$F = Q - Q_{low}/(Q_{high} - Q_{low}) \quad (2)$$

where $Q_{low}$ and $Q_{high}$ correspond to Q values obtained in the presence of zero or saturating oligo probe, respectively. This treatment assumes that the fraction of triple-helix in the absence of OLIGOTRIP must be zero, and that the fraction of triple-helix approaches 1.0 in binding reactions containing saturating concentrations of OLIGOTRIP. Values of apparent association constant ($K_a$) are obtained by least squares fit of the data to the binding isotherm:

$$F = ([OLIGOTRIP]^n)(K_a^n)/\{1 + ([OLIGOTRIP]^n(K_a^n)\} \quad (3)$$

where [OLIGOTRIP] is the concentration of OLIGOTRIP and n is the Hill coefficient (Cantro et al., in Biophysical Chemistry, W.H. Freeman, New York, 1980; p. 864).

B. Sequence specific equilibrium binding by OLIGOTRIPs.

The sequence specificity of (anti-TA)$_n$ OLIGOTRIP in different targets is tested by DNA footprinting (Jayasena & Johnston, Nucl. Acids Res. 20: 5279–5288, 1992). Dimethyl sulfate (DMS) methylates DNA at 7-G and the presence of a Hoogsteen base-paired third strand sterically prevents the reaction. Therefore, the degree of protection of a G can be used to determine the stability of a three stranded complex at specific sequences. At the same time, the effect of temperature (5°–40° C. at 5° C. steps), salt (0.05, 0.10, 0.20, 0.50 and 1.0 M NaCl, and 0.01, 0.02 and 0.05M $MgCl_2$), pH (6.0, 6.5, 7.0, 7.5, 8.0) and DNA affinity binding cations (50 μM distamycin, 50 μM spermine, 50 μM ethidium) on triplex formation can also determined. Controls with poly (dT)$_n$ are used for comparison.

C. Sequence specific blocking of endonuclease.

In order to determine if an OLIGOTRIP can compete with proteins for recognition sites, its ability to block endonuclease digestion at a specific restriction site is tested using our previously published procedure (Maher III, et al., Biochemistry 29: 8820–8826, 1990). As an example, OLIGOTRIP poly(anti-TA)$_{12}$ incubated with duplex target (the OLIGOTRIP is designed to form a triple helix motif at a selected restriction endonuclease binding site, such as DraI) for various periods of time (0, 5, 30, 60 and 120 min.) using optimized conditions (as determined in section B above) prior to adding DraI restriction enzyme. The OLIGOTRIP anti-(TA)$_{12}$ overlaps with half of the DraI recognition site, thereby inhibiting the activity of DraI endonuclease. For comparison of the OLIGOTRIP to the traditional triple helix motifs, the same experiment is performed with d(T)$_{12}$ and d(A)$_{12}$. One strand is end-labeled in order to provide information on the position of strand cutting. The use of a non-denaturing gel to determine the cutting efficiency of DraI is not possible because of the presence of the OLIGOTRIP or poly d(T)$_{12}$ or d(A)$_{12}$, which affects the mobility of the $^{32}$P-labeled DNA on a non-denaturing gel. The ability to cut the DNA therefore is determined on 20% denaturing acylamide gels by comparing the relative quantity of uncut to cut DNA in the absence and presence of the potential third strand. In order to achieve this goal, conditions are established so that about 50–70% of the duplex is cut in the absence of any potential third strand.

If the results of the foregoing analysis are unclear due to the use of a small oligomer target, the target sequence, with the appropriate ends, can be synthesized and inserted into pBR322 using the EcoR1 (location, 4359) and HindIII (location, 29) cloning sites. As pBR322 has 3 natural DraI sites (locations, 3230, 3249, 3941), it would then be quite easy to determine if the OLIGOTRIP can block endonuclease digestion of only the site that is embedded in an OLIGOTRIP binding domain.

D. Sequence specific methylation of DNA by a MNU-OLIGOTRIP.

Poly(anti-TA)$_{12}$ OLIGOTRIP with a 5'-MNU functionality is incubated with duplexes designed to have one strand comprising G's flanking the OLIGOTRIP binding site, and having that strand labeled. The methylation at 7-G is followed by electrophoresis on polyacrylamide sequencing gels, using neutral thermal hydrolysis and piperine to generate strand breaks at 7-mG. It is expected that only duplex targets with uninterrupted homo-(dA) sequences will be efficiently methylated and the methylation should occur adjacent to the OLIGOTRIP binding site. The methylation pattern will also show whether the OLIGOTRIP occupies the two potential orientations within its binding site. Therefore, the quantitative and qualitative nature of the methylation patterns will provide evidence that the OLIGOTRIP delivered the $CH_3N_2^+$ to the DNA target.

EXAMPLES 11–14

Effects of OLIGOTRIPs on SV40 T Antigen Function and DNA Replication

The following four examples demonstrate the capacity of the OLIGOTRIPs of the present invention to block the activity of DNA binding proteins at specific sequences, using endonuclease digestions and SV40 DNA polymerization endpoints. One such DNA binding protein is the large T antigen of SV40 virus. the SV40 DNA replication system is used for four reasons:

1) the virus has been intensely studied in many laboratories, and the origin of DNA replication for SV40 is known (Challberg & Kelly, Ann. Rev. Biochem. 58: 671, 1989; Simmon et al., J. Virol. 64: 1973, 1990);

2) a traditional triple helix strategy has already been successfully applied to SV40 replication in a cell culture system (Birg et al., Nucleic Acids Res. 18: 2901, 1990);

3) there is good cell-free system to study SV40 DNA replication (Li & Kelly, Proc. Natl. Acad. Sci. USA 81: 6973, 1984); and 4) the SV40 virus depends on the host for all replicative functions with the exception of the T antigen, which is a viral gene product.

To better understand these concepts, a brief description of the SV40 T antigen and the SV40 DNA replication system is set forth below.

The viral T antigen is absolutely essential for initiation of SV40 DNA replication (reviewed in Borowiec et al., Cell 60: 181, 1990). The initial step in the pathway of SV40 DNA replication is binding of the large hexameric T antigen structure to DNA sequence controlling elements which comprise the ori, which is the specific region of the SV40 DNA genome that controls the initiation of replication of the entire viral genome. Of the three binding sites of T antigen, binding site II is absolutely essential for initiating DNA replication. This binding site constitutes the core ori for replication. The core ori includes three critical domains: the central domain containing two direct repeats of a "GAGGC" sequence which is the site to which T antigen binds; a 10 base-pair region partially overlapping an imperfect inverted repeat called the early palindrome; and a 17 base-pair region rich in adenines and thymines called the "AT-tract." When the T antigen binds to DNA at the central CAGGC region, structural distortions are induced into ori DNA, a result which causes the double strands in the early palindrome element to open up, generating the site at which the genome begins to replicate. Synthetic oligomers which are complementary to the central GAGGC region and to the early palindrome regions effectively block the DNA binding and the enzymatic (helicase) activities of the T antigen. The sequences of the early palindrome and the central GAGGC region are presented below:

Early palindrome: 5'-CACTACTTCTGGATAGCTC (Sequence I.D. No. 5)

Central region: 5'-AGAGGCCGAGGCGGCCTCGGCCTC (Sequence I.D. No. 6)

EXAMPLE 11

Effect of OLIGOTRIPs on ori Binding by T Antigen

The following is exemplary of the capacity of selectively designed OLIGOTRIPs to bind to specific DNA sequences and to block cellular activities dependent on the gene activity of those DNA sequences.

DNA binding reactions are performed using the plasmid PJLO (Li & Kelly, 1984, supra), in which the HindIII/SphI fragment of SV40 DNA (nucleotides 5171–5128) is inserted into the pKP45 vector DNA. Plasmid pJLO is propagated and the HindIII/SphI restriction fragment is purified. The restriction fragment is labeled with E. coli polymerase I Klenow fragment. OLIGOTRIPs 3'-anti(TA-AT-CG-TA-TA-CG-TA-GC-GC-AT-AT-TA-AT-GC) (corresponding to underlined portion of Sequence I.D. No. 5) and 3'-ANTI (AT-GC-AT-GC-GC-CG-CG-GC-AT-GC-GC-CG-GC-GC) (corresponding to underlined portion of Sequence I.D. No. 6) are annealed to form the triple helical structure. DNA binding assays using this labeled triple helix and immunoaffinity purified T antigen are performed according to published procedures (Stillman, et al., EMBO J. 4: 2933, 1985) using nitrocellulose filter binding followed by polyacrylamide gel electrophoresis to demonstrate the binding capacity of the T antigen. As positive controls, the end-labeled restriction fragment duplex is used alone. An OLIGOTRIP that has no binding site in the SV40 plasmid is also used as a negative control. The efficiency of inhibition by OLIGOTRIP directed to the early palindrome site is compared to the inhibition when directed to the central region.

EXAMPLE 12

OLIGOTRIP Inhibition of the ori Specific Unwinding Activity of T antigen Upon binding to the central region, T antigen unwinds the ori DNA, a process which is ATP-dependent. The DNA unwinding ability of T antigen is different when it contacts a triple helical template that includes the OLIGOTRIP strand bound to the early palindrome region. When provided with a single-stranded template and a complementary primer, T antigen displaces the primer without any specificity for the DNA sequence at that site. However, the unwinding activity on fully double-stranded DNA is restricted to targeted templates which contain the SV40 ori sequence. The ori specific DNA unwinding assay (Dean et al., Proc. Natl. Acad. Sci. USA 84: 3643, 1987) is utilized, in which the unwinding is reflected by the appearance in electrophoretic gels of faster migrating supercoiled forms of the labeled DNA evident in reactions containing T antigen. This assay is carried out, generally, as follows:

1) end-label an OLIGOTRIP which has the sequence 3'-anti(TA-AT-CG-TA-TA-CG-TA-GC-GC-AT-AT-TA-AT-GC) (corresponding to underlined portion of Sequence I.D. No. 5);
2) permit the OLIGOTRIP to bind to the early palindrome region to form the triple helix with the plasmid pJLO; and
3) measure the ori specific unwinding activity.

In complementary experiments, the PJLO plasmid is labeled and forms triple helix with unlabeled OLIGOTRIPs. T antigen produced in HeLa cells is used, using the AdSVR 284 adenovirus-SV40 hybrid virus, since T antigen expressed in E coli has been shown to be unable to perform the ori-dependent unwinding reaction.

EXAMPLE 13

SV40 DNA Synthesis in vitro on Triple Helical DNA

Studies are designed to measure the ability of HeLa cell extracts and immunoaffinity purified T antigen to synthesize DNA when provided with plasmid pJLO blocked at the ori region by the formation of a triple helix with OLIGOTRIP at the early palindrome and central binding regions, respectively, using 3'-anti(TA-AT-CG-TA-TA-CG-TA-GC-GC-AT-AT-TA-AT-GC) (corresponding to underlined portion of Sequence I.D. No. 5) and 3'-anti(AT-GC-AT-GC-GC-CG-CG-GC-AT-GC-GC-CG-GC-GC) (corresponding to underlined portion of Sequence I.D. No. 6). DNA synthesis is monitored by agarose gel electrophoresis of product DNA followed by autoradiography. Positive controls for the synthesis reaction include plasmid pJLO-d4, in which a 4 base pair deletion at the origin abolishes T antigen dependent DNA replication.

EXAMPLE 14

Effect of Synthetic Oligomers on SV40 Replication in vivo

In this example, the inhibition of SV40 DNA synthesis by triple helix formation at the ori is demonstrated by incubation of monkey CV1 cells with the synthetic oligomers followed by infection of cells with the SV40 virus. Various concentrations of the synthetic oligomers are used. Viral DNA synthesis is measured by Southern blot analysis at various times after infection, using [$^{32}$P] or [$^{35}$S]-labeled SV40 DNA as a probe according to previously published procedures (Birg et al., Nucleic Acids Res. 18: 2901, 1990). The amount of hybridization is quantified by scanning the blot on a Betascope 603 (Betagen) radioanalytical imager.

EXAMPLE 15

Inhibition of Endonuclease Digestion at Specific Restriction Sites as a Method to Confirm Efficacy of OLIGOTRIPs As described in a previous Example, a complementary method to determine efficacy of the OLIGOTRIPs is to determine their ability to block endonuclease digestion at specific restriction sites based on the sequence flanking the endonuclease recognition site. Accordingly, a 5238 base pair parvovirus plasmid, cps-CPV (S. Rhode, J. Virol. 54: 630, 1985) contains two HindIII cleavage sites (AAGCTT) at position 154 and 815. The flanking sequences at the two sites are GTATGT<u>AAGCTT</u>CCAGGA (Sequence I.D. No. 7) and ACGACG<u>AAGCTT</u>ACGCTG (Sequence I.D. No. 8), respectively. The EcoR1 linearized plasmid is incubated with OLIGOTRIP 3'-anti (GC-TA-AT-TA-GC-TA-(AT)$_2$-(CG)$_2$-AT-(GC)$_2$-AT) (Corresponding to Sequence I.D. No. 7) for various periods of time (5 min, 30 min, 1 hr, 2 hr) prior to adding the restriction enzyme. The number (0, 1 or 2) and position (154 and/or 815) of the sites cut by the HindIII are determined by electrophoresis on an agarose gel. Cutting occurs only at the 815-position, which is not targeted by the OLIGOTRIP.

EXAMPLE 16

Use of OLIGOTRIPs to Inhibit Parvovirus Transcription in vivo

Parvovirus H-1 has two promoter genes, P4 and P38, which express a nonstructural gene and a capsid protein gene, respectively. These genes are organized in tandem and overlap on the linear genome. Both promoters are highly dependent on a gene sequence called a "TATA box", which is the binding site for the transcription factor "TF-II-D". An OLIGTRIP that targets the TATA box is tested for its antiviral activity by direct assay of its effects on the transcription of the P4 gene of parvovirus H-1; this is done by primer extension analysis. The P4 TATA box sequence is: 5'-CTGTATATAAGCAG (Sequence I.D. No. 9); therefore, the OLIGOTRIP to be used to form a triple helical structure to this target sequence is 3'-anti(<u>GC-TA-AT-TA-AT-TA-AT-AT-GC-CG-AT-GC</u>) (corresponding to underlined portion of Sequence I.D. No. 9). The transcription factor TF-II-D protects about 20 bp from DNAse-I digestion. When the OLIGOTRIP binds to the parvovirus P4 TATA box with specificity, this is shown in vivo by comparing the inhibition of 3$^1$-anti(GC-TA-AT-TA-AT-TA-AT-AT-GC-CG-AT-GA) against its target, the parvovirus P4 promoter, relative to the SV40 early promoter, which has a different TATA box sequence: TATTTATGCAGAGG (Sequence I.D. No. 10)

Similarly, the P38 promoter TATA box is targeted and, because P38 is expressed at higher levels than P4, even fewer infected cells are necessary for the assay. The P38 TATA box sequence is: 5'-CTCCTATAAATTCGC (Sequence I.D. No. 11). This differs from the P4 sequence and it provides a second test of the specificity of the OLIGOTRIP described above. A comparison of the ratios of the P4 to P38 transcripts as affected by dose of OLIGOTRIP is a measure of the specificity of its binding.

The P38 promoter has a second target for inhibition, which is an upstream element termed the "TAR" (5'-TTGGTTGGTGAAGAA) (Sequence I.D. No. 12), that is required for the transactivation of the P38 promoter by the NS1 protein. Nucleotides critical to transactivation have been identified by site-directed mutagenesis. Specific inhibition of this target causes an increase in the ratio of P4 transcripts to P38 transcripts in primer extension assays and in Northern blots when binding to downstream sites is not inhibitory.

It is also possible to test for inhibition of transcription elongation by OLIGOTRIP binding at any site within the template using the same methods and Northern blot analysis. The P38 promoter is embedded in the transcribed region of the NS1 gene expressed by the P4 promoter. Thus, OLIGOTRIP binding to the P38 TATA box, which is downstream from the P4 promoter, is used to detect inhibition of transcript elongation in the same experiment as inhibition of transcription initiation. The P38 TATA box is about 1700 nucleotides from the cap site of P4 transcripts. Inhibition of elongation at P38 produces truncated P38 transcripts that are not polyadenylated or correctly spliced. Such transcripts have a short half-life and, thus, are found in reduced abundance.

Inhibition of transcription by the OLIGOTRIP is correlated to antiviral effects in an in vitro cell killing assay. Cultured, susceptible target cells are plated in 96-well microtiter dishes and infected at a multiplicity-of-infection of 1 viral particle per 10 cells, to about 1 viral particle per 100 cells. Various concentrations of OLIGOTRIP are added to the wells. After an incubation time of 3 days, the cell viability is measured. This assay is sensitive because the virus has to go through several rounds of infection to amplify the viral titer to a multiplicity of infection sufficient to generate the signal by killing a significant proportion of the cells.

EXAMPLE 17

Use of OLIGOTRIPs to Inhibit Parvovirus DNA Replication in vitro

Using a Vaccinia virus expression vector to produce NS1, an assay to show that a protein designated "rep" binds the terminal hairpin and carries out a site-specific cleavage of the DNA in vitro is done for the parvovirus H-1 NS1 protein. The substrate is an end-labeled hairpin fragment containing the cleavage site. The products of the cleavage are assayed by denaturing gel electrophoresis. This reaction is inhibited by using an OLIGOTRIP synthesized to specifically bind to the site of cleavage for the 3' hairpin (or for the 5'-hairpin). The sequence at the 3' cleavage site is 5'-CAGTTC TAAAAAT*GATAAGCG (Sequence I.D. No. 13), where "*" indicates the cleavage site and the underlined region is the OLIGOTRIP, and the sequence at the 5'-hairpin cleavage site is 5'-CTACTGTCT*ATTCAGTTGAC (Sequence I.D. No. 14). Accordingly, OLIGOTRIP 3'-anti(TA-[AT]$_5$-TA-GC-AT-TA-AT-AT-GC-CG-GC) (corresponding to underlined portion of Sequence I.D. No. 13) is used in these experiment, and in the in vivo experiment detailed below.

Since the rep protein binds the terminal hairpin in a structure-specific manner and saturates the stem until the cleavage site is bound, inhibition of binding more proximal to the end inhibits the replication as well. As a result, alternative sites for OLIGOTRIP binding more proximal to the end are also available for testing. When the normal cleavage site is blocked by OLIGOTRIP, then cleavage at a less preferred site occurs. This is detected in both the in vitro and in vivo assays.

EXAMPLE 18

Use of OLIGOTRIPs to Inhibit Parvovirus DNA Replication in vivo

The OLIGOTRIP prepared above for in vitro experiments has specificity for the rep cleavage site that is required for DNA replication in vivo. NB cell cultures, synchronized by isoleucine starvation, are infected with parvovirus in the presence of a 20 hour block with aphidicolin. Infection proceeds synchronously after reversal of the aphidicolin block. Infected cultures are treated with various doses of OLIGOTRIP and viral DNA extracted and quantitated by Southern blotting at 10 hours post reversal of the block. A 35 mm dish with 1 ml of medium provides enough signal to demonstrate the reduced yield of viral DNA, as confirmed by ethidium bromide staining of gels after electrophoresis.

Parvovirus H-1 causes a fatal infection of newborn Syrian hamsters or newborn Eppley-strain Wistar rats. Thus, the efficacy of OLIGOTRIPs directed against pravovirus targets is exhibited in animals by the protection these OLIGOTRIPs afford to newborn animals which receive a systemic infusion of the OLIGOTRIP prior to receiving an inoculation of the lethal virus. The endpoints used are animal survival times and titers of virus in specific tissues, such as the liver and blood.

In practicing the present invention, one of ordinary skill in the art, with the aid of the present disclosure and the use of state of the art computer aided molecular modeling, can effect various changes, substitutions of equivalents and other alterations to the compositions herein set forth, in order to effectively carry into practice the teachings of this invention. While the present invention has been described in conjunction with preferred embodiments and specific examples, the description is not meant to limit it. Therefore, the protection granted by Letters Patent should not be limited except by the language of the claims set forth below.

What is claimed is:

1. A substituted quinazoline having the following formula:

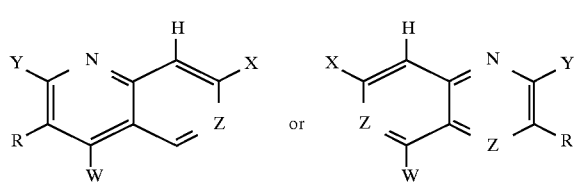

wherein X and Y are the same or different and are selected from the group consisting of —H, —NRR', —OR and —SR; Z represents C—R; R and R' can be the same or different and are selected from the group consisting of hydrogen, lower-alkyl, carboxyl and $C_6$–$C_{12}$ hydrocarbon aryl, and wherein W is a substituent that enables linkage of said substituted quinazoline to another substituted quinazoline and is selected from the group consisting of ribose and deoxyribose.

2. A substituted quinazoline having the formula of claim 1 wherein W is a 2'-deoxy-beta-D-ribofuranos-1-yl.

3. A substituted quinazoline of claim 2 selected from the group consisting of 2-amino-4-(2'-deoxy-beta-D-ribofuranos-1-yl)-7-hydroxyquinazoline and 2-amino-5-(2'-deoxy-beta-D-ribofuranos-1-yl)-7-hydroxyquinazoline.

4. A substituted quinoline having the following formula:

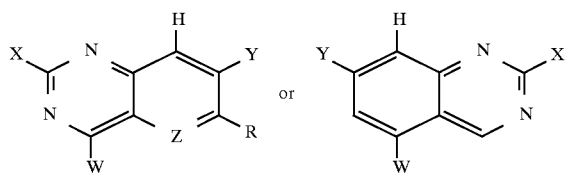

or wherein Z is C—R; X is selected from the group consisting of H, $CO_2^-$, $CS_2^-$, and $SO_3^-$; Y is selected from the group consisting of NRR', OR, and SR; R and R' are the same or different and are selected from the group consisting of hydrogen, lower-alkyl, carboxyl and $C_6$–$C_{12}$ hydrocarbon aryl, and wherein W is a substituent that enables linkage of said substituted quinoline with another substituted quinoline and is selected from the group consisting of ribose and deoxyribose.

5. A substituted quinoline having the formula of claim 4 wherein W is a 2'-deoxy-beta-D-ribofuranos-1-yl.

6. A substituted quinoline of claim 5 selected from the group consisting of 2-amino-4-(2'-deoxy-beta-D-riboFuranos-1-yl)-7-carboxyquinoline and 2-amino-5-(2'-deoxy-beta-D-ribofuranos-1-yl)-7-carboxyquinoline.

* * * * *

UNITED STATES PATENT AND TRADEMARK OFFICE
CERTIFICATE OF CORRECTION

PATENT NO.   : 5,844,110
DATED        : December 1, 1998
INVENTOR(S)  : Barry I. Gold It is certified that error appears in the above-identified patent and that said Letters Patent is hereby corrected as shown below:

Column 41,
Line 3, the formulas:

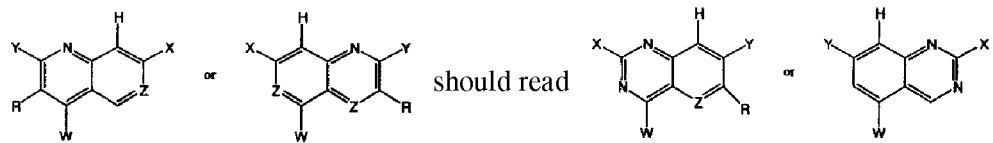

Column 43,
Line 2, the formulas:

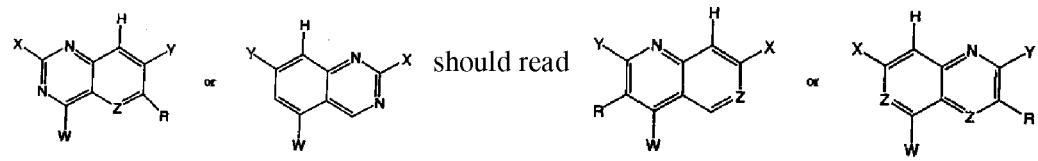

Signed and Sealed this

Twenty-eighth Day of June, 2005

JON W. DUDAS
*Director of the United States Patent and Trademark Office*